US009085463B2

(12) United States Patent
Farrell et al.

(10) Patent No.: US 9,085,463 B2
(45) Date of Patent: Jul. 21, 2015

(54) WATER-SOLUBLE FUNCTIONALIZED FULLERENES

(75) Inventors: Mark Farrell, Pittsburgh, PA (US); Michelle Guaragno, McKees Rocks, PA (US)

(73) Assignee: Marelle, LLC, Pittsburgh, PA (US)

( * ) Notice: Subject to any disclaimer, the term of this patent is extended or adjusted under 35 U.S.C. 154(b) by 433 days.

(21) Appl. No.: 13/351,376

(22) Filed: Jan. 17, 2012

(65) Prior Publication Data

US 2012/0183468 A1 Jul. 19, 2012

Related U.S. Application Data

(60) Provisional application No. 61/433,338, filed on Jan. 17, 2011.

(51) Int. Cl.
*C01B 31/00* (2006.01)
*C07C 67/08* (2006.01)
(Continued)

(52) U.S. Cl.
CPC ............ *C01B 31/0206* (2013.01); *B82Y 30/00* (2013.01); *B82Y 40/00* (2013.01); *C07C 29/12* (2013.01); *C07C 29/62* (2013.01); *C07C 35/44* (2013.01); *C07C 45/70* (2013.01); *C07C 46/00* (2013.01); *C07C 49/84* (2013.01); *C07C 50/26* (2013.01);
(Continued)

(58) Field of Classification Search
CPC .... C07C 69/587; C07C 67/08; C07C 69/013; C07C 29/62; C07C 35/52; C07C 46/00; C07C 50/26; C07C 45/70; C07C 49/84; C07C 303/02; C07C 309/25; C07C 231/12; C07C 233/25

USPC .............. 423/445 B; 977/734–741, 842–848
See application file for complete search history.

(56) References Cited

U.S. PATENT DOCUMENTS 5,177,248 A 1/1993 Chiang et al.
5,294,732 A 3/1994 Chiang et al.
(Continued)

FOREIGN PATENT DOCUMENTS

DE 4312475 A1 10/1994
DE 4421207 A1 12/1995
(Continued)

OTHER PUBLICATIONS

Taylor, et al., The chemistry of fullerenes, Nature 1993; 363: 685-693.*
(Continued)

*Primary Examiner* — Daniel C McCracken
(74) *Attorney, Agent, or Firm* — The Webb Law Firm

(57) ABSTRACT

Provided herein are water-soluble, functionalized fullerenes, and processes for producing water-soluble, functionalized fullerenes. The process includes sulfonating a fullerene in an acidic solution comprising sulfuric acid to produce a sulfonated fullerene, isolating the sulfonated fullerene from the acidic solution without neutralizing the acidic solution, reacting the sulfonated fullerene with hydrogen peroxide to form a reaction product, and isolating a polyhydroxylated fullerene from the reaction product produced from reacting the sulfonated fullerene with the hydrogen peroxide. The process of producing water-soluble fullerenes further includes functionalizing a polyhydroxylated fullerene with one or more pendant functional groups by reacting the polyhydroxylated fullerene with one or more functional group precursors.

12 Claims, 35 Drawing Sheets

(51) Int. Cl.

| | | |
|---|---|---|
| *C07C 17/07* | (2006.01) | |
| *C07D 495/04* | (2006.01) | |
| *C07J 5/00* | (2006.01) | |
| *C07K 17/14* | (2006.01) | |
| *C07C 233/25* | (2006.01) | |
| *C07C 233/43* | (2006.01) | |
| *C07C 69/017* | (2006.01) | |
| *C07C 49/753* | (2006.01) | |
| *C07C 49/84* | (2006.01) | |
| *C07C 231/12* | (2006.01) | |
| *C01B 31/02* | (2006.01) | |
| *B82Y 30/00* | (2011.01) | |
| *B82Y 40/00* | (2011.01) | |
| *C07C 29/62* | (2006.01) | |
| *C07C 35/44* | (2006.01) | |
| *C07C 69/013* | (2006.01) | |
| *C07C 69/52* | (2006.01) | |
| *C07C 69/587* | (2006.01) | |
| *C07C 303/02* | (2006.01) | |
| *C07C 45/70* | (2006.01) | |
| *C07C 46/00* | (2006.01) | |
| *C07C 50/26* | (2006.01) | |
| *C07C 29/12* | (2006.01) | |

(52) U.S. Cl.
CPC ............... *C07C 67/08* (2013.01); *C07C 69/013* (2013.01); *C07C 69/52* (2013.01); *C07C 69/587* (2013.01); *C07C 231/12* (2013.01); *C07C 303/02* (2013.01); *C07D 495/04* (2013.01); *C07J 5/0053* (2013.01); *C07C 2101/16* (2013.01); *C07C 2104/00* (2013.01)

(56) References Cited

U.S. PATENT DOCUMENTS

| | | | |
|---|---|---|---|
| 5,416,188 A | 5/1995 | Chiang et al. | |
| 5,635,581 A | 6/1997 | Chiang et al. | |
| 5,648,523 A * | 7/1997 | Chiang ..................... | 562/100 |
| 5,688,486 A | 11/1997 | Watson et al. | |
| 5,739,376 A | 4/1998 | Bingel | |
| 5,994,410 A | 11/1999 | Chiang et al. | |
| 6,020,523 A | 2/2000 | Chiang | |
| 6,046,361 A | 4/2000 | Chiang | |
| 6,162,926 A | 12/2000 | Murphy et al. | |
| 6,204,391 B1 | 3/2001 | Friedman et al. | |
| 6,399,785 B1 | 6/2002 | Murphy et al. | |
| 6,448,412 B1 | 9/2002 | Murphy et al. | |
| 6,695,974 B2 | 2/2004 | Withers et al. | |
| 6,884,405 B2 | 4/2005 | Ryzhkov | |
| 7,001,580 B2 | 2/2006 | Baran, Jr. et al. | |
| 7,226,699 B2 | 6/2007 | Uetake | |
| 7,252,812 B2 | 8/2007 | Yakobson et al. | |
| 7,371,479 B2 | 5/2008 | Nuber | |
| 7,511,217 B1 | 3/2009 | Roscheisen et al. | |
| 7,547,429 B2 | 6/2009 | Nakamura et al. | |
| 2003/0220518 A1 | 11/2003 | Bolskar et al. | |
| 2004/0062971 A1 | 4/2004 | Nuber | |
| 2004/0140201 A1 | 7/2004 | Horikawa | |
| 2004/0224203 A1 | 11/2004 | Bhamidipati et al. | |
| 2005/0058675 A1 | 3/2005 | Wilson et al. | |
| 2005/0098776 A1 | 5/2005 | Geckeler et al. | |
| 2005/0221184 A1 | 10/2005 | Naruto et al. | |
| 2006/0073370 A1 | 4/2006 | Krusic et al. | |
| 2006/0115513 A1 | 6/2006 | Hossainy et al. | |
| 2006/0134095 A1 | 6/2006 | Ito et al. | |
| 2008/0213324 A1 | 9/2008 | Zhou et al. | |
| 2008/0219917 A1 | 9/2008 | Koruga | |
| 2009/0076171 A1 | 3/2009 | Zhao et al. | |
| 2009/0118527 A1 | 5/2009 | Nakamura et al. | |
| 2009/0302029 A1 | 12/2009 | Krishna et al. | |
| 2010/0028402 A1 | 2/2010 | Dobrovolskaia et al. | |

FOREIGN PATENT DOCUMENTS

| | | |
|---|---|---|
| JP | 5182818 A | 7/1993 |
| JP | 624720 A | 2/1994 |
| JP | 200280414 A | 3/2002 |
| JP | 2004168752 A | 6/2004 |
| JP | 2007296593 A | 11/2007 |
| JP | 200984497 A | 4/2009 |
| WO | 2006028297 A1 | 3/2006 |
| WO | 2006065243 A1 | 6/2006 |
| WO | 2008096763 A1 | 8/2008 |
| WO | 2009069164 A1 | 6/2009 |

OTHER PUBLICATIONS

Bolskar et al., "First soluble M@C60 Derivatives Provide Enhanced Access to Metallofullerenes and Permit in Vivo Evaluation of Gd@C60[C(COOH)2]10 as a MRI Contrast Agent," J. Am. Chem. Soc., 2003, pp. 5471-5478, vol. 125.

Chiang et al., "Multi-hydroxy Additions onto C60 Fullerene Molecules," J. Chem. Soc., Chem. Commun., 1992, pp. 1791-1793.

Chiang et al., "Evidence of Hemiketals Incorporated in the Structure of Fullerols Derived from Aqueous Acid Chemistry," J. Am. Chem. Soc., 1993, pp. 5453-5457, vol. 115.

Chiang et al., "Versatile Nitronium Chemistry for C60 Fullerene Functionalization," J. Am. Chem. Soc., 1992, pp. 10154-10157, vol. 114.

Chiang et al., "Efficient Synthesis of Polyhydroxylated Fullerene Derivatives via Hydrolysis of Polycyclosulfated Precursors," J. Org. Chem., 1994, pp. 3960-3968, vol. 59.

Chiang et al., "Synthesis of Fullerols as Polyhydroxylated Fullerene Derivatives," Mat. Res. Soc. Symp. Proc., 1992, pp. 285-292, vol. 247.

Chiang et al., "Efficient One-Flask Synthesis of Water-Soluble [60]Fullerenols," Tetrahedron, 1996, pp. 4963-4972, vol. 52, No. 14.

Diederich, "Covalent fullerene chemistry," Pure & Appl. Chem., 1997, pp. 395-400, vol. 69, No. 3.

Fileti et al., "Effects of hydroxyl group distribution on the reactivity, stability and optical properties of fullerenols," Nanotechnology, 2008, 8 pp., vol. 19.

Fuller, "Preparation of Polyfluoroaromatic Compounds by the Reaction of Perhalogeno-aromatic Compounds with Potassium Fluoride in Sulpholan," published on Jan. 1, 1965 on http://pubs.rsc.org., pp. 6264-6267.

Iwashita et al., "AlCl3-Mediated Mono-, Di, and Trihydroarylation of [60]Fullerene," Angew. Chem. Int. Ed., 2007, pp. 3513-3516, vol. 46.

Kokubo et al., "Facile Synthesis of Highly Water-Soluble Fullerenes More Than Half-Covered by Hydroxyl Groups," ACS Nano, 2008, pp. 327-333, vol. 2, No. 2.

Li et al., " C60 Fullerol Formation catalysed by Quaternary Ammonium Hydroxides," J. Chem. Soc., Chem. Commun., 1993, pp. 1784-1785.

Matsubayashi et al., "One-step Synthesis of Water-soluble Fullerols Bearing Nitrogen-containing Substituents," Fullerenes, Nanotubes and Carbon Nanostructures, 2009, pp. 440-456, vol. 17.

Olah et al., "Chlorination and Bromination of Fullerenes, Nucleophilic Methoxylation of Polychlorofullerenes and Their Aluminum Trichloride Catalyzed Friedel-Crafts Reaction with Aromatics to Polyarylfullerenes," J. Am. Chem. Soc., 1991, pp. 9385-9387, vol. 113.

Schneider et al., "Formation of Fullerols via Hydroboration of Fullerene-C60," J. Chem. Soc., Chem. Commun., 1994, pp. 463-464.

Selig et al., "Fluorinated Fullerenes," J. Am. Chem. Soc., 1991, pp. 5475-5476, vol. 113.

Shi et al., "Synthesis and antioxidative properties of polyphenol-fullerenes," Chinese Science Bulletin, Nov. 2001, pp. 1790-1792, vol. 46, No. 21.

Shoulders, "C60: Synthesis and Biological Activity of Water-Soluble Fullerenes," Raines Group, Oct. 5, 2006, pp. 1-54, Powerpoint presentation.

(56) References Cited

OTHER PUBLICATIONS

Tebbe et al., "Synthesis and Single-Crystal X-ray Structure of a Highly Symmetrical C60 Derivative, C60Br24," Science, May 8, 1992, pp. 822-825, vol. 256.

Wang et al., Novel and Efficient Synthesis of Water-Soluble [60]Fullerenol by Solvent-Free Reaction, Synthetic Communications: An International Journal for Rapid Communication of Synthetic Organic Chemistry, 2005, pp. 1803-1808, vol. 35:13.

Wienk et al., "Efficient Methano[70]fullerene/MDMO-PPV Bulk Heterojunction Photovoltaic Cells," Angew. Chem. Int. Ed., 2003, pp. 3371-3375, vol. 42.

Yang et al., "Design and synthesis of fullerene-based amino acids," ACS National Conference, Philadelphia, PA, Aug. 22-26, 2004, 3 pp.

Yin et al., "Synthesis of water-soluble C60 derivatives and their scavenging free radical activity," Science in China, Feb. 2002, pp. 54-59, vol. 45 No. 1.

* cited by examiner

WATER-SOLUBLE FUNCTIONALIZED FULLERENES

CROSS REFERENCE TO RELATED APPLICATIONS

The present application claims priority to U.S. Provisional Patent Application No. 61/433,338 filed on Jan. 17, 2011 entitled "Water-Soluble Fullerenes", the entire disclosure of which is herein incorporated by reference.

BACKGROUND OF THE INVENTION

Provided herein are methods of producing fullerene derivatives, and in particular, a method of producing polyhydroxylated fullerenes and functionalized polyhydroxylated fullerenes.

A fullerene is a carbon compound composed entirely of carbon, in the form of a hollow sphere, ellipsoid, or tube. Spherical fullerenes are sometimes referred to as "buckyballs." Spherical fullerenes generally have both pentagonal and hexagonal faces. The spherical $C_{60}$ "buckminsterfullerene" is a common type of fullerene.

Since the discovery of fullerenes, various types of fullerene derivatives have been synthesized. Studies have shown that fullerene derivatives can exhibit important biological activities. An example of a fullerene derivative is a fullerene having a plurality of hydroxyl functional groups attached thereto. These polyhydroxylated fullerenes can be further modified to form functionalized polyhydroxylated fullerenes. Polyhydroxylated fullerenes and functionalized polyhydroxylated fullerenes are water-soluble and retain their water-soluble characteristic. Polyhydroxylated fullerenes and functionalized polyhydroxylated fullerenes may be used in any environment or application in which water-solubility is desired or otherwise required. Examples of such environments or applications include, without limitation, the following: biomedical, pharmaceutical, and medicinal chemistry applications (e.g., anti-oxidants, anti-inflammatory agents, diagnostic agents, therapeutic agents, and targeted drug delivery systems), dermatologic and cosmetic applications, nanotechnology applications (e.g., proton conductors and pigments), food chemistry (e.g., supplements to food and drink), and clothing applications (e.g., additions to fabrics).

Current methods of producing hydroxylated fullerenes and functionalized hydroxylated fullerenes suffer from low hydroxylation yields and process contamination, for example, by sodium ions. Thus, there is a need for a simple process of producing highly hydroxylated, high purity fullerene derivative compositions.

SUMMARY

According to one embodiment of the methods described herein, a process of producing water-soluble fullerenes is provided. The process comprises sulfonating a fullerene in an acidic solution comprising sulfuric acid to produce a sulfonated fullerene, isolating the sulfonated fullerene from the acidic solution without neutralizing the acidic solution, reacting the sulfonated fullerene with hydrogen peroxide to form a reaction product, and isolating a polyhydroxylated fullerene from the reaction product produced from reacting the sulfonated fullerene with the hydrogen peroxide. For example, and without limitation, the fullerene is a $C_{60}$ spherical fullerene.

The acidic solution comprising sulfuric acid may include any additional ingredients that assist in the sulfonation reaction. For example, and without limitation, the acidic solution is fuming sulfuric acid, comprising sulfuric acid and $SO_3$. According to other non-limiting embodiments, the acidic solution comprising sulfuric acid further comprises $HNO_3$, or the fuming sulfuric acid also comprises $P_2O_5$, and/or $V_2O_5$. In one non-limiting embodiment, the sulfonated fullerene is isolated by centrifugation, and the hydroxylated fullerene is isolated by a precipitation step performed in an organic solvent. The organic solvent, for example, is a mixture of organic solvents that includes an alcohol, an aliphatic organic compound (a carbon-containing compound, an example of which is a hydrocarbon comprising only carbons and hydrogens), such as a saturated aliphatic hydrocarbon, and/or an ether. In another non-limiting example, the organic solvent is a mixture of isopropanol, hexane, and diethyl ether. The organic solvent mixture comprises a volume ratio range of about 10-70:10-70:10-70 of alcohol to aliphatic hydrocarbon to ether. In a non-limiting example, the sulfonated fullerene comprises a ratio of sulfate groups to carbon atoms of at least (4-7):60, and the polyhydroxylated fullerene comprises a ratio of hydroxyl groups to carbon atoms of at least 2:3.

Alcohols are organic compounds in which an —OH group is attached to a saturated carbon and can be primary, secondary or tertiary, and may be or may comprise linear, branched, or cyclic structures. Non-limiting examples of alcohols include: $C_{1-3}$, $C_{1-4}$ or $C_{1-6}$ alcohols, for example, methanol, ethanol, 1-propanol, 2-propanol, t-butanol, 1-butanol, 2-butanol, and cyclic alcohols such as hexanol. Monohydric alcohols comprise one —OH group and may in certain instances be preferred to polyhydric alcohols which comprise more than one —OH group. Aliphatic compounds are acyclic or cyclic non-aromatic organic compounds including saturated and unsaturated compounds. Saturated aliphatic hydrocarbons may be preferred in certain instances, non-limiting examples of which include, n-, iso- and cyclic hydrocarbons such as methane, ethane, propane, cyclopropane, n-butane, isobutane, cyclobutane, pentane, cyclopentane, hexane, cyclohexane, etc.

In yet another non-limiting embodiment, the process of producing water-soluble fullerenes further comprises functionalizing a polyhydroxylated fullerene with one or more pendant functional groups by reacting the polyhdroxylated fullerene with one or more functional group precursors. The one or more pendant functional group precursors may include a hydrogen halide. The step of functionalizing a polyhydroxylated fullerene with one or more pendant functional groups may also include reacting the polyhdroxylated fullerene with one or more functional group precursors in the presence of a Lewis acid catalyst. The one or more functional group precursors reacted with the polyhydroxylated fullerene in the presence of a Lewis acid catalyst may be chosen, for example, from an aromatic compound, a fatty acid, a peptide, a corticosteroid, an anti-oxidant, and a vitamin. For example, and without limitation, the functionalized polyhydroxylated fullerene comprises a ratio of at least 1:60 functional groups to carbon atoms, and a ratio of at least 2:3 hydroxyl groups to carbon atoms.

As another non-limiting embodiment, the process of producing water-soluble fullerenes further comprises functionalizing a polyhydroxylated fullerene with one or more pendant functional groups by reacting a polyhydroxylated fullerene with two or more functional group precursors, thereby producing a composition comprising polyhydroxylated fullerenes functionalized with two or more functional groups. For example, and without limitation, the two or more functional group precursors are chosen from an aromatic compound, a fatty acid, a peptide, a corticosteroid, an antioxidant, a vitamin, and hydrogen halide.

Additionally, in a non-limiting embodiment, a method of making a water-insoluble composition soluble in an aqueous solution is provided. The method comprises reacting a water-insoluble composition containing a carboxylic acid group with a polyhydroxylated fullerene, thereby linking the water-insoluble composition to the polyhydroxylated fullerene to produce a fullerene conjugate.

Further provided herein, in another non-limiting embodiment, is a water-soluble polyhydroxylated fullerene having the general formula: R—(OH)$_x$ wherein R is a fullerene and x is a number of at least ⅔ the number of carbon atoms in R.

Also provided herein, in a non-limiting embodiment, is a water-soluble functionalized polyhydroxylated fullerene having the general formula: R—(R')$_y$(OH)$_x$ wherein R is a fullerene, R' is a functional group, x is a number of at least ⅔ the number of carbon atoms in R, and y is a number in the range from about 1% to about 7% of the number of carbon atoms in R. For example, and without limitation, R' is chosen from an aromatic compound, a fatty acid ester, a peptide, a corticosteroid, an anti-oxidant, a vitamin, and a halogen. Alternatively, the R' may be chosen from prednisone, arachidonic acid, biotin, avobenzone, glutathione, propanil, hydrocortisone, linoleic acid, α-linolenic acid, Coenzyme Q$_{10}$, an avobenzone/glutathione mixture, and mixtures thereof.

In a further embodiment, a process of producing a polyhydroxylated fullerene is provided that does not require a sulfonation step. In the process, a fullerene is reacted with greater than 30% H$_2$O$_2$, thereby producing a polyhydroxylated fullerene. According to one embodiment of the process, the fullerene is reacted with at least 50% H$_2$O$_2$.

DESCRIPTION OF THE PREFERRED EMBODIMENT(S)

Figure 1:
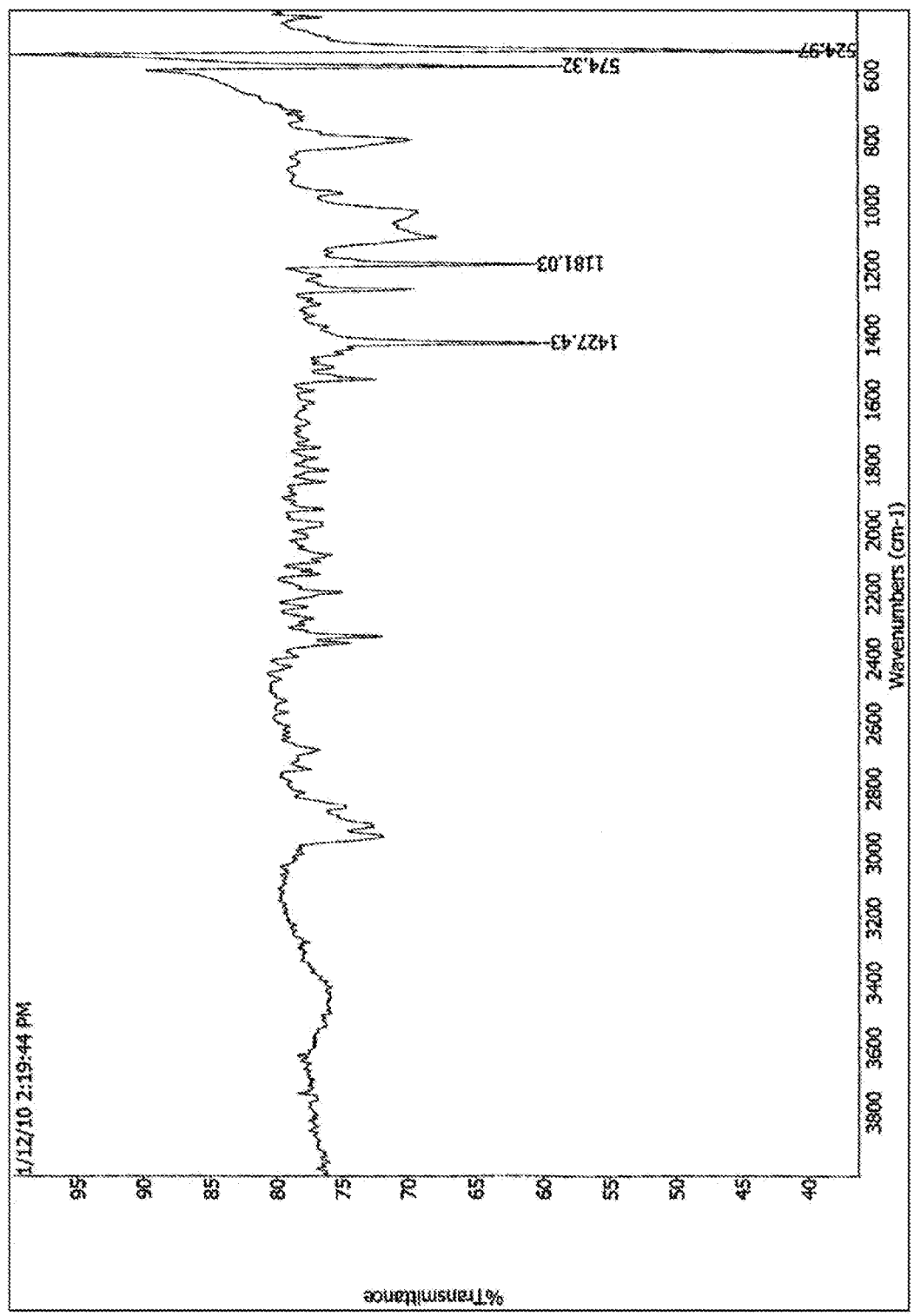
FIG. 1 illustrates an Infrared Spectrum of C$_{60}$ Fullerene.

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and claims are approximations that may vary depending upon the desired properties sought to be obtained by the present invention. At the very least, and not as an attempt to limit the application of the Doctrine of Equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

The use of the singular includes the plural and plural encompasses singular, unless specifically stated otherwise. In addition, in this application, the use of the term "or" means "and/or" unless specifically stated otherwise, even though "and/or" may be explicitly used in certain instances.

As used herein, "fullerene" refers to a compound composed entirely of carbon, in the form of a hollow sphere, ellipsoid, or tube. Each carbon atom is connected by one double bond and two single bonds to other carbon atoms. Spherical fullerenes generally have a mixture of pentagonal faces and hexagonal faces, non-limiting examples which include $C_{60}$, $C_{70}$, $C_{72}$, $C_{76}$, $C_{84}$, and $C_{100}$ spherical fullerenes, including isomorphs thereof. Tubular fullerenes often comprise only hexagonal faces and may comprise very large numbers of carbon atoms in one molecule, which, depending on the method of manufacture, can be highly polydisperse.

As used herein, a "functional group precursor" refers to a compound or composition that will react covalently with the fullerene to produce a fullerene with pendant groups derived from the functional group precursor. As would be recognized by those skilled in the art, various portions of the functional group precursor will be retained on the surface of the fullerene as pendant functional groups, depending on the chemistry of the linking/conjugation process used to functionalize the fullerene.

As used herein, a "functionalized fullerene" refers to a fullerene comprising one or more pendant functional groups attached to the surface of the fullerene and which is/are derived from functional group precursors after the functional group precursor is reacted with the fullerene.

Provided herein are water-soluble, functionalized fullerenes, and processes for producing water-soluble, functionalized fullerenes. The processes described herein are capable of rendering compounds water-soluble without changing their chemical and physical properties. Where the fullerenes are functionalized with an anti-oxidant functional group precursor, certain compounds are seen to be 100 to 300 times better as an anti-oxidant and have a higher level of UVA and UVB absorption properties. The processes include easy isolation steps and are applicable to a broad range of compounds.

As noted above, a fullerene is a compound composed entirely of carbon. Each carbon atom is connected by one double bond and two single bonds to other carbon atoms. As a result, a fullerene is susceptible to electrophilic addition, which is a reaction where a double bond is broken and two new single bonds are formed. The first step in creating the water-soluble fullerene is to produce a sulfonated fullerene through electrophilic addition. As used herein, a "sulfonated fullerene" refers to a fullerene with one or more sulfate groups attached to the fullerene surface.

The sulfonated fullerene can be made by various methods. For example, a fullerene can be reacted in an ultrasonic bath with sulfuric acid and nitric acid to produce a sulfonated fullerene. Alternatively, the sulfonated fullerene can be produced by reacting a fullerene with fuming sulfuric acid and phosphorus pentoxide. In yet another method, a fullerene can be reacted with vanadium pentoxide and the reaction product of sulfuric acid and nitric acid. In one embodiment, shown in the examples below, a fullerene is reacted with fuming sulfuric acid, a mixture of sulfur acid and sulfur trioxide, also referred to as oleum. Without any intent to be bound by this theory, the sulfuric acid carries a positive charge and can break the double bonds located on the fullerene. Once the double bonds are broken, sulfate from the sulfuric acid attaches to the fullerene creating a sulfonated fullerene.

After the reaction is complete, the sulfonated fullerene is then isolated from the reaction mixture without neutralizing the acidic solution. Isolating the sulfonated fullerene can be performed by centrifugation and filtration. In one non-limiting embodiment, the sulfonated fullerene is isolated by ultracentrifugation and decantation with diethyl ether. The resulting structure is a fullerene with greater than 6% of the carbon atoms having a sulfate group attached thereto. Because a neutralizing step is not used, contamination from sodium and potassium ions is avoided. Reference to a number of pendant hydroxyl or functional groups on a fullerene or a percentage of carbons of the fullerene that are substituted with a hydroxyl group or functional group are averages and, as one of ordinary skill in the art would recognize, not intended to represent numbers or percentages on every molecule, but on a population of molecules.

The sulfonated fullerene serves as a precursor in the formation of a polyhydroxylated fullerene. As used herein, a "hydroxylated fullerene" refers to a fullerene with one or more pendant hydroxyl groups. A "polyhydroxylated fullerene" refers to a fullerene with a plurality of pendant hydroxyl groups. A "fullerenol" is a hydroxylated or polyhydroxylated fullerene.

In hydroxylating the fullerene, reactive sites on the sulfonated fullerene are oxidized to create the polyhydroxylated fullerene. As used herein, "oxidation" refers to the loss of one or more electrons in an element, compound, or chemical substituent/subunit. In the hydroxylation step, hydrogen peroxide is used to oxidize the reactive sites on the sulfontated fullerene. The hydrogen peroxide typically has a concentration in the range of up to and greater than 50% by mass hydrogen peroxide in solution. Without any intent to be bound by this theory, the hydroxyl radicals from the hydrogen peroxide initially replace the sulfonate groups attached to the fullerene and the hydroxyl radicals react with carbon-carbon double bonds of the fullerene, thus attaching hydroxyl groups to the fullerene molecule.

In an alternate embodiment, a fullerene is directly hydroxylated with $H_2O_2$. In this embodiment, there is no need for sulfonation, so the sulfonation step is omitted. A fullerene is reacted in greater than 30% $H_2O_2$, such as 50% mass $H_2O_2$ or greater concentrations, for a time period effective to polyhydroxylate the fullerene. The reaction is performed at between 60° C. and 80° C., for example at 70° C., for example and without limitation, 7 days or longer or 10 days or longer, such as 7 or 14 days.

The polyhydroxylated fullerene is isolated, for example, by precipitating the polyhydroxylated fullerene in an organic solvent or an organic solvent mixture comprising two or more organic solvents. As used herein, an "organic solvent" refers to a solvent that is generally immiscible with water, such as non-polar and polar aprotic solvents. Non-limiting examples of organic solvents include diethyl ether, diisopropyl ether, ethyl acetate, pentane, hexane, heptane, cyclohexane, benzene, toluene, and isopropanol.

In one non-limiting example, an organic solvent mixture comprising an alcohol, an aliphatic organic (carbon-containing) compound, and an ether is used to precipitate the polyhydroxylated fullerene out of the oxidation reaction mixture described above. As used herein, an "aliphatic organic compound" refers to acyclic or cyclic non-aromatic organic compounds including saturated and unsaturated compounds. Alkanes (alkyl) are saturated hydrocarbons. Alkanes may be preferred in certain instances as aliphatic organic compounds, non-limiting examples of which include, n-, iso-, and cyclic hydrocarbons such as methane, ethane, propane, cyclopropane, n-butane, isobutane, cyclobutane, pentane, cyclopentane, hexane, cyclohexane, etc. Hydrocarbons are organic compounds that include primarily the elements hydrogen and carbon. Organic compounds may also include other elements in addition to carbon and hydrogen, such as, but not limited to, halogens, metallic elements, nitrogen, oxygen, and/or sulfur. Alcohols are saturated or unsaturated organic compounds in which an —OH group is attached to a saturated carbon, they can be primary, secondary, or tertiary and may be or may comprise linear, branched or cyclic structures. Non-limiting examples of alcohols include: $C_{1-3}$, $C_{1-4}$ or $C_{1-6}$ alcohols, for example methanol, ethanol, 1-propanol, 2-propanol, t-butanol, 1-butanol, 2-butanol, pentanols, hexanols, including cyclic alcohols such as cyclohexanol. Monohydric alcohols comprise one —OH group and may in certain instances be preferred to polyhydric alcohols which comprise more than one —OH group. As used herein, an "ether" refers to a compound comprising an ether group (a C—O—C linkage) having the structure R—O—R', where R and R' are organic groups, for example and without limitation, one or more of alkenyl, alkynyl, cycloalkyl, aryl, heteroaryl or heteroalicyclic groups. In certain embodiments R and R' are independently $C_{1-6}$ alkyl.

The organic solvent mixture can include a volume ratio range of about 10-70:10-70:10-70 of alcohol:aliphatic organic compound:ether (alcohol to aliphatic organic compound to ether). In one non-limiting embodiment, the organic solvent mixture has a ratio of 10:12:7 of alcohol to hydrocarbon to ether. In one embodiment, the alcohol is isopropanol, the aliphatic organic compound is hexane, and/or the ether is diethyl ether. Based on elemental analysis and infrared spectroscopy, the resulting polyhydroxylated fullerene has a ratio of hydroxyl groups to carbons of at least or greater than 2:3 (that is (≥2):3 or (>2):3). Thus, in the specific example of $C_{60}$, the fullerene would have at least 40, 41, or greater numbers of hydroxyl groups attached to its surface. The abundance of hydroxyl groups attached according to the described process yields a fullerene having a high level of water solubility and which also does not have sodium or potassium contamination as seen in other processes. It should be noted with respect to the number of hydroxyl, sulfate, or functional groups said to be attached to a fullerene, the numbers are average numbers calculated by art-recognized methods. Thus, for example, a $C_{60}$ fullerene said to comprise 4 sulfate groups is actually a population of fullerenes with approximately 4 sulfate groups per molecule on the average, with a range of sulfates per fullerene molecule ranging, for example and without limitation, from 4-7 or from 1-10 sulfate groups per fullerene molecule.

To produce functionalized fullerenes, a polyhydroxylated fullerene is reacted with one or more pendant functional group precursors to produce a water-soluble, functionalized polyhydroxylated fullerene with pendant functional groups retaining their desired physical and chemical properties. As used herein, a "functionalized polyhydroxylated fullerene" refers to a fullerene with at least one hydroxyl group and at least one other chemical group attached to the fullerene surface.

In one embodiment, the polyhydroxylated fullerene is reacted with one or more functional group precursors in the presence of a Lewis acid catalyst. Non-limiting examples of Lewis acid catalysts include $BF_3$, HF, $BH_3$, $MgBr_2$, $SnCl_4$, $TiCl_4$, $FeCl_3$, $AlCl_3$, $MeAlCl_2$, $Me_2AlCl$, and $LiClO_4$. In a non-limiting embodiment, the polyhydroxylated fullerene is reacted with one or more functional group precursors in the presence of a Lewis acid catalyst for a period of about 2 days to about 5 days or greater. The resulting functionalized polyhydroxylated fullerene comprises a ratio of at least 1:60 (that is ≥1:60) functional groups to carbon atoms. For example, a $C_{60}$ fullerene comprises 2 or more functional groups.

An aromatic compound is a functional group precursor that can be reacted with a polyhydroxylated fullerene to produce an aromatic-functionalized polyhydroxylated fullerene. As used herein, an "aromatic compound" refers to any organic compound which has a conjugated ring structure. An "aromatic-functionalized polyhydroxylated fullerene" refers to a fullerene with at least one hydroxyl group and at least one aromatic compound attached to the fullerene surface. Non-limiting examples of aromatic compounds include resveratrol, propanil, avobenzone, benzene, toluene, xylene, trimethyl benzene, tetramethyl benzene, ethyl benzene, propyl benzene, diphenyl methane, naphthalene, and methyl naphthalene.

To attach the aromatic compound to the fullerene, the aromatic compound is reacted with the polyhydroxylated fullerene in the presence of a Lewis acid catalyst, such as $BF_3$. Without any intent to be bound by this theory, the Lewis acid catalyst turns the polyhydroxylated fullerene into an electrophile, thereby allowing the aromatic compound to attach to the polyhydroxylated fullerene. The resulting aromatic-functionalized polyhydroxylated fullerene has a ratio of hydroxyl groups to carbon atoms of at least or greater than 2:3, and at least a ratio of aromatic functional groups to carbon atoms of at least 1:60. For example, a $C_{60}$ fullerene would have an average of 40 or more pendant hydroxyl groups and one or more functional groups.

A fatty acid ester-functionalized polyhydroxylated fullerene can be produced by reacting the polyhydroxylated fullerene with a fatty acid. As used herein, a "fatty acid" is a carboxylic acid with a long, unbranched carbon chain. Fatty acids may be saturated or unsaturated. A non-limiting example of a fatty acid is an omega-3 fatty acid such as α-linolenic acid, docosahexaenoic acid (DHA), and eicosapentaenoic acid (EPA), or an omega-6 fatty acid such as α-linolenic acid and arachidonic acid. As used herein, a "fatty acid ester" refers to a compound formed between a fatty acid and a hydroxyl-containing compound. A "fatty acid ester-functionalized polyhydroxylated fullerene" refers to a fullerene with at least one hydroxyl group and at least one fatty acid ester attached to the fullerene surface.

In one embodiment, a fatty acid, such as α-linolenic acid, is reacted with the polyhydroxylated fullerene in the presence of a Lewis acid catalyst such as $BF_3$. The resulting fatty acid ester-functionalized polyhydroxylated fullerene can have a ratio of hydroxyl groups to carbon atoms of at least or greater than 2:3, and a ratio of fatty acid ester groups to carbon atoms of at least 1:60.

In yet another embodiment, the polyhydroxylated fullerene is reacted with a hydrogen halide, in the form of a concentrated acid, to produce a halogen-functionalized polyhydroxylated fullerene. As used herein, the term "halogen" refers to fluorine (F), chlorine (Cl), bromine (Br), iodine (I), and astatine (At). A "halogen-functionalized polyhydroxylated fullerene" refers to a fullerene with at least one hydroxyl group and at least one halogen attached to the fullerene surface. The resulting halogen-functionalized polyhydroxylated fullerene has a ratio of hydroxyl groups to carbon atoms of at least or greater than 2:3, and a ratio of halogen-functional groups to carbon atoms of at least 1:60.

In addition to the above functionalized polyhydroxylated fullerenes, also provided are peptide-functionalized polyhydroxylated fullerenes, corticosteroid-functionalized polyhydroxylated fullerenes, anti-oxidant-functionalized polyhydroxylated fullerenes, and vitamin-functionalized polyhydroxylated fullerenes. As used herein, a "peptide" refers to two or more amino acids joined to each other by peptide bonds or modified peptide bonds. Non-limiting examples of peptides include glutathione, ophthalmic acid, carnosine, anserine, kyotorphin, melanostatin, norophthalmic acid, and thyrotropin. The resulting peptide-functionalized polyhydroxylated fullerene has a ratio of hydroxyl groups to carbon atoms of at least or greater than 2:3, and a ratio of peptide-functional groups to carbon atoms of at least 1:60.

A "corticosteroid" refers to a naturally occurring product of the adrenal cortex, or a synthetic analog thereof, as are recognized in the pharmaceutical and medical arts. Non-limiting examples of a corticosteroid that can be attached to the surface of the polyhydroxylated fullerene include: hydrocortisone-type corticosteroids, such as prednisone, hydrocortisone, methylprednisolone, and prednisolone; acetonides, such as triamcinolone acetonide, budesonide, and fluocinonide; betamethasone types, such as betamethasone, dexamethasone, and fluocortolone; and esters, such as hydrocortisone-17-valerate, betamethasone valerate, betamethasone dipropionate, hydrocortisone-17-butyrate, fluticasone propionate, betamethasone dipropionate, triamcinolone acetonide, and mometasone furoate. The resulting corticosteroid-functionalized polyhydroxylated fullerene has a ratio of hydroxyl groups to carbon atoms of at least or greater than 2:3, and a ratio of corticosteroid-functional groups to carbon atoms of at least 1:60.

As used herein, a "vitamin" refers to any of various organic substances essential in minute quantities to the nutrition of most animals, for example as coenzymes and precursors of coenzymes in the regulation of metabolic processes. Vitamins can be soluble in water or insoluble in water. Water-insoluble vitamins are made soluble after they are attached to the water-soluble polyhydroxylated fullerene. Non-limiting examples of vitamins used in the present invention include biotin, coenzyme $Q_{10}$, and vitamins A, D, E, and K. The resulting vitamin-functionalized polyhydroxylated fullerene has a ratio of hydroxyl groups to carbon atoms of at least or greater than 2:3, and a ratio of vitamin-functional groups to carbon atoms of at least or greater than 1:60.

An "anti-oxidant" refers to a synthetic or natural substance that can prevent, delay, or otherwise inhibit the oxidation of another compound or biological substance. Non-limiting examples of anti-oxidants that can be attached to the surface of the polyhydroxylated fullerene include linoleic acid, and linolenic acid. Other examples include, without limitation, vitamins such as vitamin C, vitamin E, tocopherols, tocotrienols, and carotenes; enzymes such as catalase, superoxide dismutase, and peroxidases; and thiols, polyphenols, resorcinol, and melatonin. The resulting anti-oxidant-functionalized polyhydroxylated fullerene has a ratio of hydroxyl groups to carbon atoms of at least or greater than 2:3, and a ratio of anti-oxidant-functional groups to carbon atoms of at least or greater than 1:60.

Polyhydroxylated fullerenes can also be reacted with two or more functional group precursors to produce a functionalized polyhydroxylated fullerene with at least two different functional groups attached to the surface of the fullerenol. One or more of the functional group precursors, e.g., as described above, can be reacted together or independently with polyhydroxylated fullerenes to form a polyfunctionalized polyhydroxylated fullerene. For instance, the polyhydroxylated fullerene can be reacted with an aromatic compound and a fatty acid in the presence of a Lewis acid catalyst to form an aromatic and fatty acid ester polyhydroxylated fullerene.

As will be appreciated from the foregoing, provided herein are functionalized polyhydroxylated fullerene compositions having the general formula of $R-(R')_y(OH)_x$, wherein R is a fullerene, R' is a functional group, OH is a hydroxyl functional group, x is a number of at least ⅔ the number of carbon atoms in R, and y is a number in the range from about 1% to about 7% of the number of carbon atoms in R. The functional group, R', can be any of the above functional groups described above including an aromatic compound, a fatty acid ester, a peptide, a corticosteroid, an anti-oxidant, a vitamin, a halogen, and mixtures thereof. As an example, R is a $C_{60}$ spherical fullerene, R' is propanil (an aromatic compound), x is 40, and y is 2.

As shown in the examples below, it was surprisingly discovered that the ability of an anti-oxidant to inhibit oxidation was significantly improved after attaching the anti-oxidant to the polyhydroxylated fullerene. The ability of a component to serve as an anti-oxidant is readily tested by a variety of methods known in the art. These analytical methods measure the radical-scavenging activity of anti-oxidants against free radicals, such as the 1,1-diphenyl-2-picrylhydrazyl (DPPH) radical. In its radical form, DPPH characteristically absorbs light at 517 nanometers (nm). This absorbance disappears as the DPPH is consumed upon reduction by an antiradical compound. The disappearance of this so-called absorbance band can be followed by spectroscopic methods allowing quantitative measurements of the compound's anti-oxidant ability.

As further shown in the examples, the functionalized polyhdroxylated fullerenes described herein exhibited superior UV absorbing abilities. The ability of a component to absorb UV light is readily tested using spectroscopic instruments, such as a UV/Vis spectrophotometer. It was found that the UV absorbing ability of the functionalized polyhdroxylated fullerenes is effective for both the UV A (400-315 nm) and UV B (315-280 nm) regions of the ultraviolet spectrum.

The following examples are presented for illustration purposes. The invention should not be considered as limited to the specific examples presented. In particular, the following examples describe production of various functionalized polyhydroxylated fullerenes. All parts are by weight unless otherwise indicated.

EXAMPLES

Example 1

Figure 2:
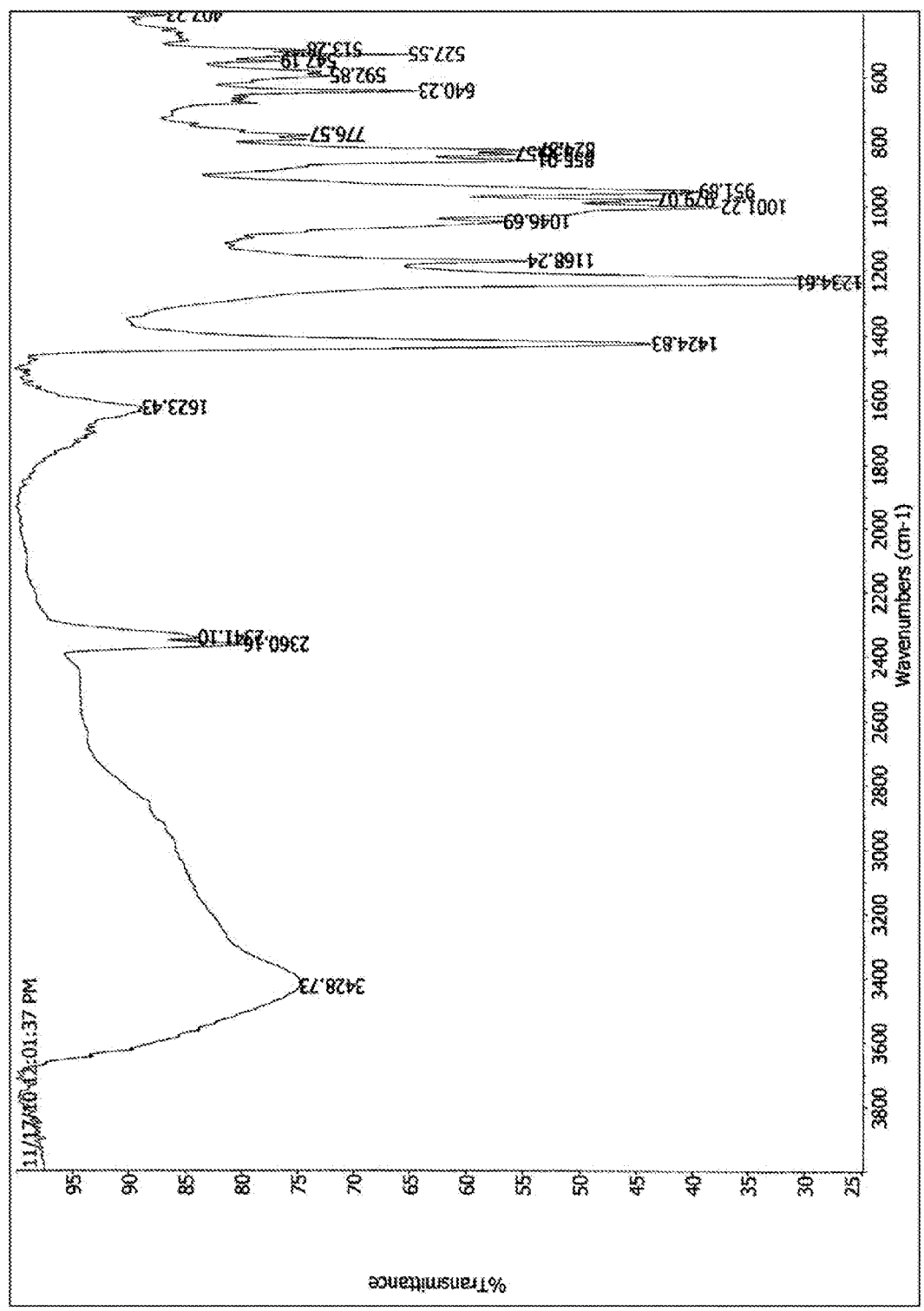
FIG. 2 illustrates an Infrared Spectrum of Sulfonated Fullerene.

Preparation of a Sulfonated Fullerene 3.5 ml of aqueous fuming sulfuric acid $H_2SO_4.SO_3$ (20% $H_2SO_4.SO_3$ by mass) was reacted with 0.200 grams of $C_{60}$ fullerene. The mixture of fuming sulfuric acid and fullerene was placed in a reaction flask, flushed with nitrogen, and then heated in a silicone oil bath. The reaction mixture was continuously stirred at a temperature in the range from about 50° C. to about 70° C. for a period of about four to about five days. At the end of the reaction process, a solid was isolated by ultracentrifugation and decantation with diethyl ether. The solid was then placed in a desiccator for about two days. Using a combination of elemental analysis and infrared spectroscopy, it was determined that the resulting product, a sulfonated fullerene, had a formula of $C_{60}(SO_4)a$ a wherein a is in the range from about 4 to about 7. Elemental analysis yielded the following results: % C 48.9, % H 1.65, % O 35.44, % S 14.09. FIG. 2 illustrates an infrared spectrum of $C_{60}$ fullerene, $C_{60}(SO_4)a$, wherein a is in the range from about 4 to about 7.

Example 2

Preparation of a Polyhydroxylated Fullerene

Figure 3:
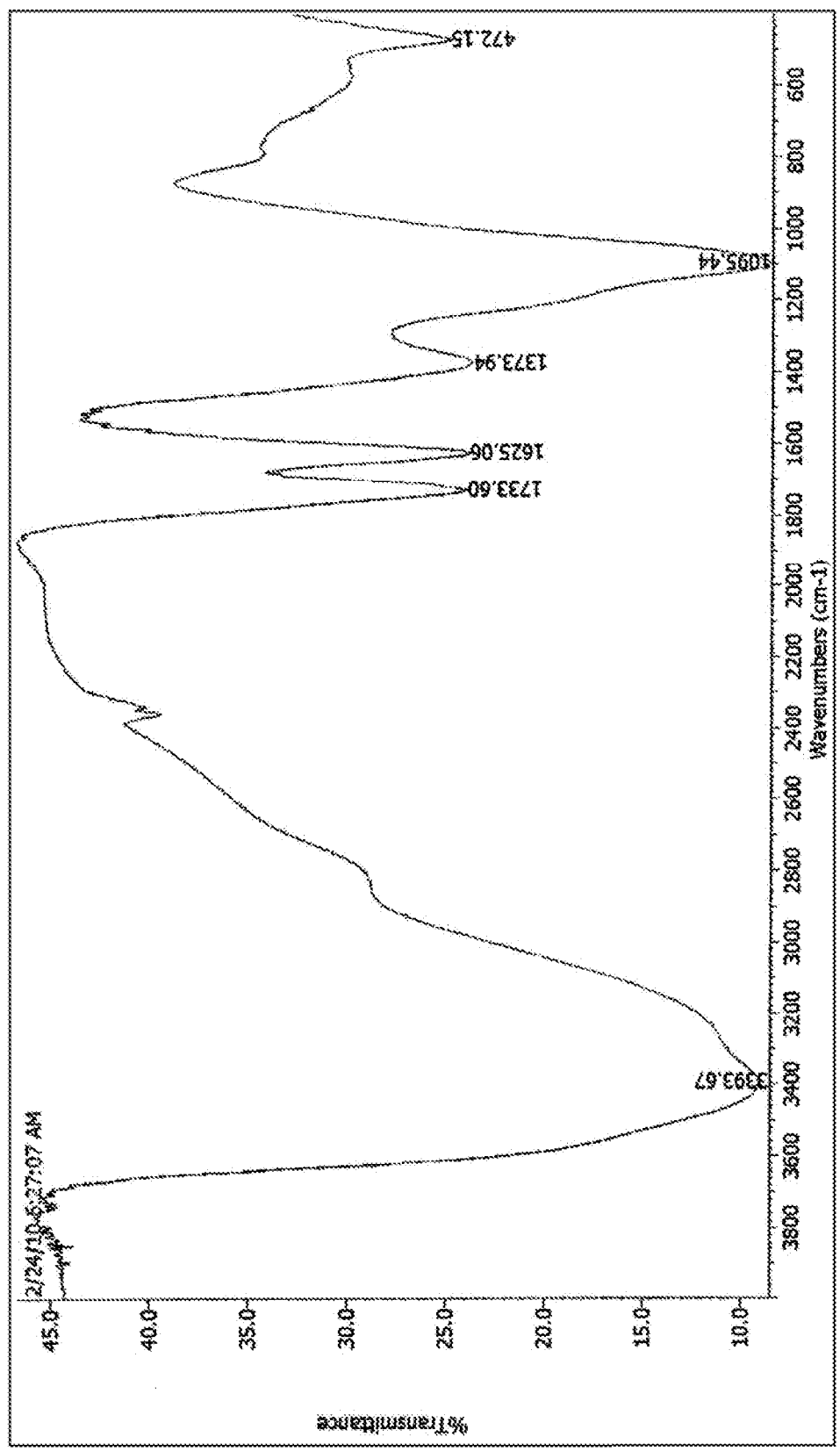
FIG. 3 illustrates an Infrared Spectrum of Polyhydroxylated Fullerene.

About 0.100 grams to about 0.200 grams of the sulfonated fullerene produced from Example 1 was reacted with 10 ml of aqueous concentrated hydrogen peroxide (30% $H_2O_2$ by mass). The reaction mixture was stirred vigorously at a temperature in the range from about 50° C. to about 70° C. for a period of about four to about five days. The reaction mixture was then added to a mixture of isopropanol, hexane, and diethyl ether in a ratio of 10:12:7 to cause a precipitate, in the form of solid crystals to form. After ultracentrifugation and decantation, the solid crystals were isolated. Using a combination of elemental analysis and infrared spectroscopy, it was determined that the resulting product, a polyhydroxylated fullerene, had a formula of $C_{60}(OH)_x$ wherein x is in the range from about 24 to about 45. The range of "x" is due to the length of the reaction time. Elemental analysis yielded the following results: % C 47.63, % H 2.79, % O 47.61, % S 0.25. FIG. 3 illustrates the infrared spectrum of the polyhydroxylated fullerene, $C_{60}(OH)_{45}$.

Figure 29:
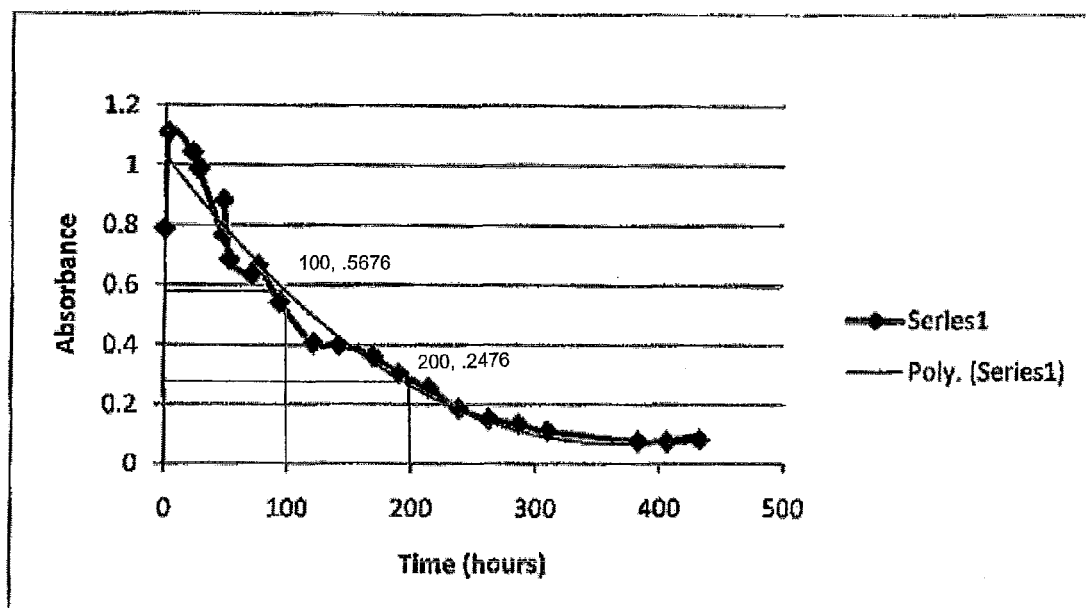
FIG. 29 illustrates an absorption-time graph, based upon ultraviolet-visible spectrophotometer absorption data, which shows the kinetics of the polyhydroxylation reaction.
Figure 30:
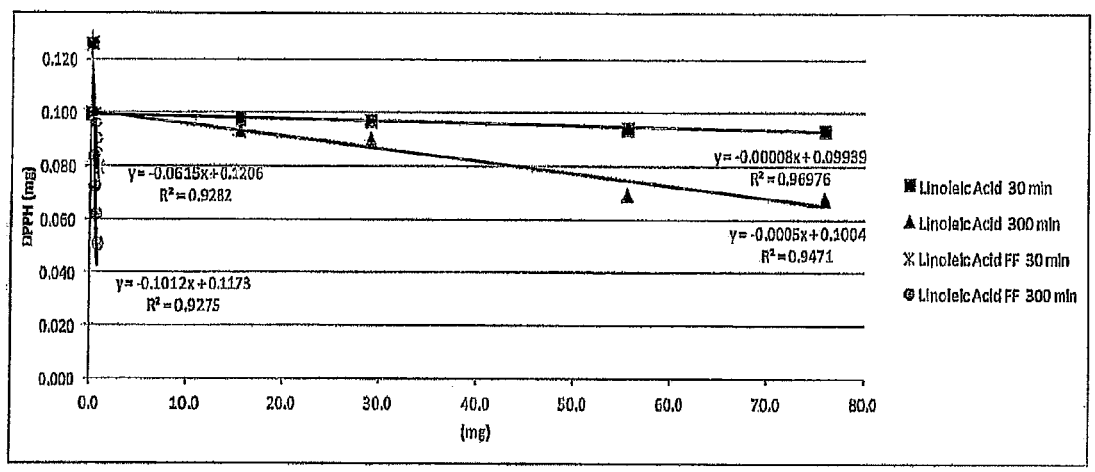
FIG. 30 illustrates the anti-oxidant potential of Linoleic Acid and Linoleic Acid Ester-functionalized Polyhydroxylated Fullerene.
Figure 31:
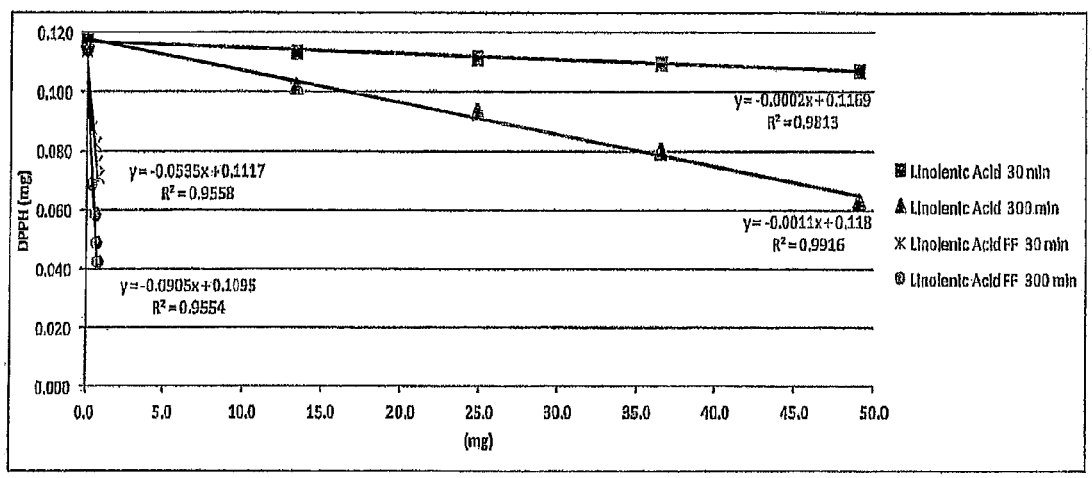
FIG. 31 illustrates the anti-oxidant potential of Linolenic Acid and Linolenic Acid Ester-functionalized Polyhydroxylated Fullerene.
Figure 32:
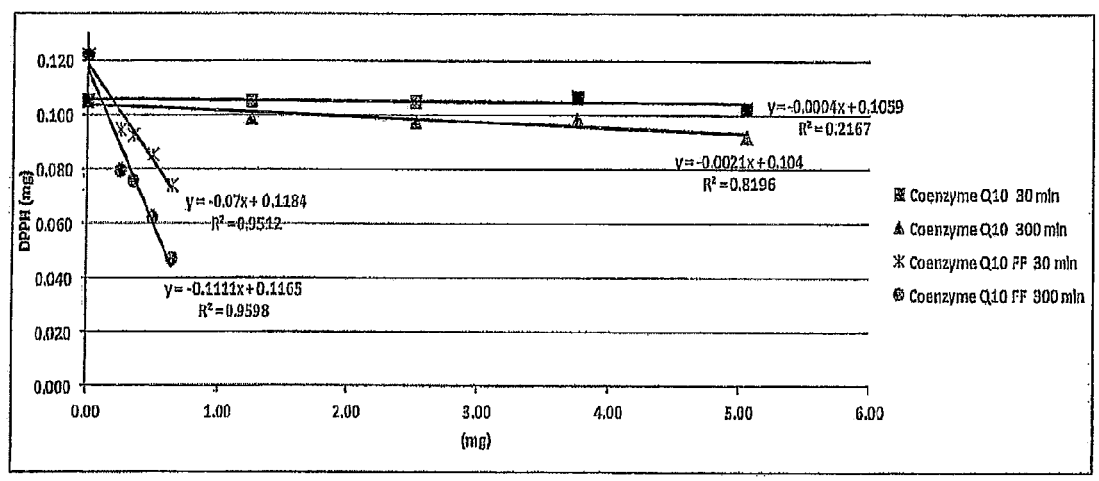
FIG. 32 illustrates the anti-oxidant potential of Coenzyme Q10 and Coenzyme Q10-functionalized Polyhydroxylated Fullerene.
Figure 33:
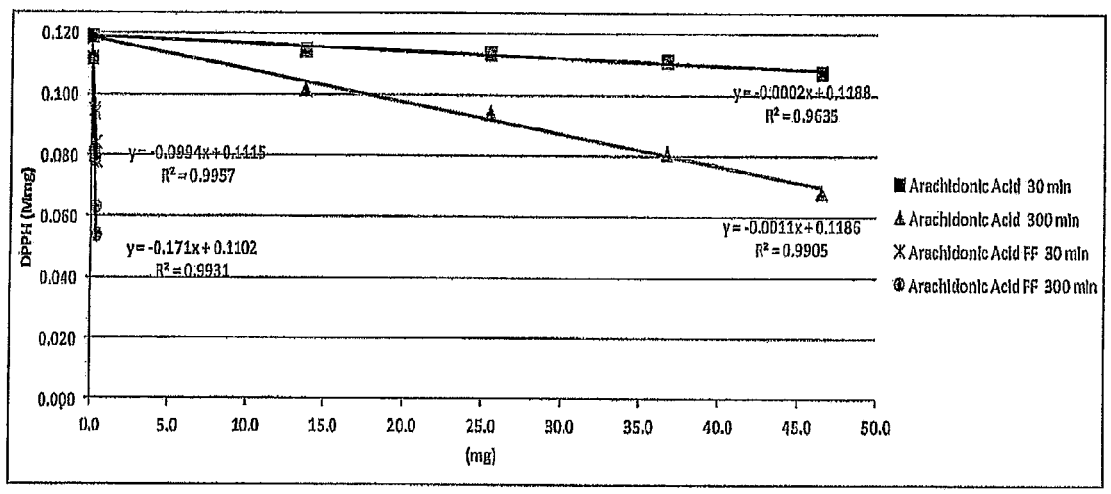
FIG. 33 illustrates the anti-oxidant potential of Arachidonic Acid and Arachidonic Acid-functionalized Polyhydroxylated Fullerene.
Figure 34:
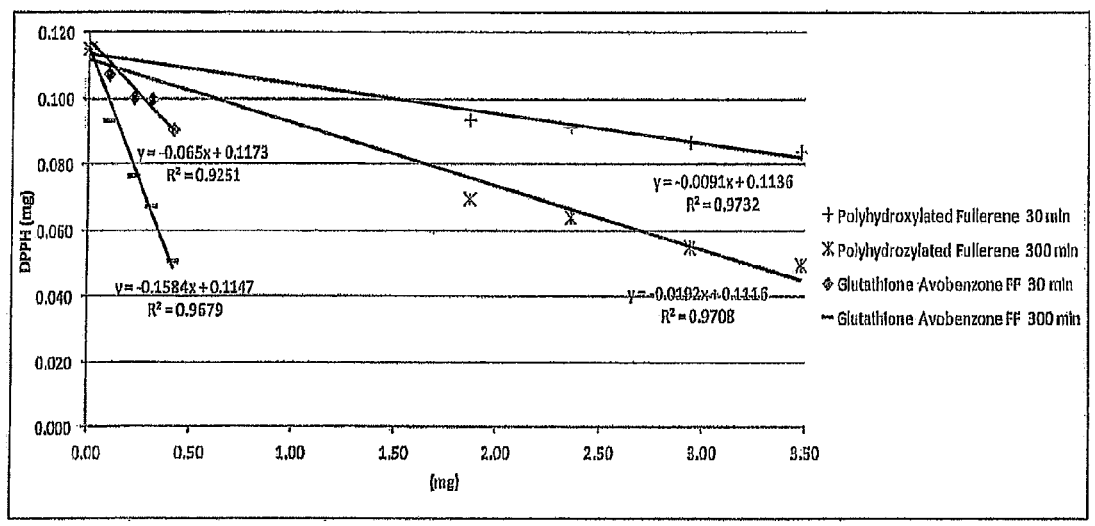
FIG. 34 illustrates the anti-oxidant potential of Polyhydroxylated Fullerene and Avobenzone/Glutathione-functionalized Polyhydroxylated Fullerene.

FIG. 29 illustrates an absorption-time graph, based upon ultraviolet-visible spectrophotometer absorption data, measured at 350 nm, which shows the kinetics of the polyhydroxylation reaction as described above. Actual data points and best fit of the data are shown. In particular, the symbol, labeled "Series 1", represents actual data points and the symbol labeled "Poly. (Series 1)" represents a graph showing the best fit of the actual data. As illustrated in FIG. 29, the data confirms that the reaction is a first order reaction with a half-life of around 100 hours (about 4.17 days) when about one-half of the maximum reaction has been achieved. Extending the reaction past this time makes the polyhydroxylated fullerene so soluble that isolation of the product becomes too difficult. The y axis is the absorbance and the x axis is time (in hours). The significance of the data as illustrated in FIG. 29, including in regard to the two actual data points at 100 hours at an absorbance of 0.6576 and at 200 hours at an absorbance of 0.2476, is that the optimum reaction time for the polyhydroxylation reaction, as described in Example 2 above, is within the range from about 4 to about 7 days (i.e., in the range from about 96 hours to about 168 hours).

Example 3

Figure 4:
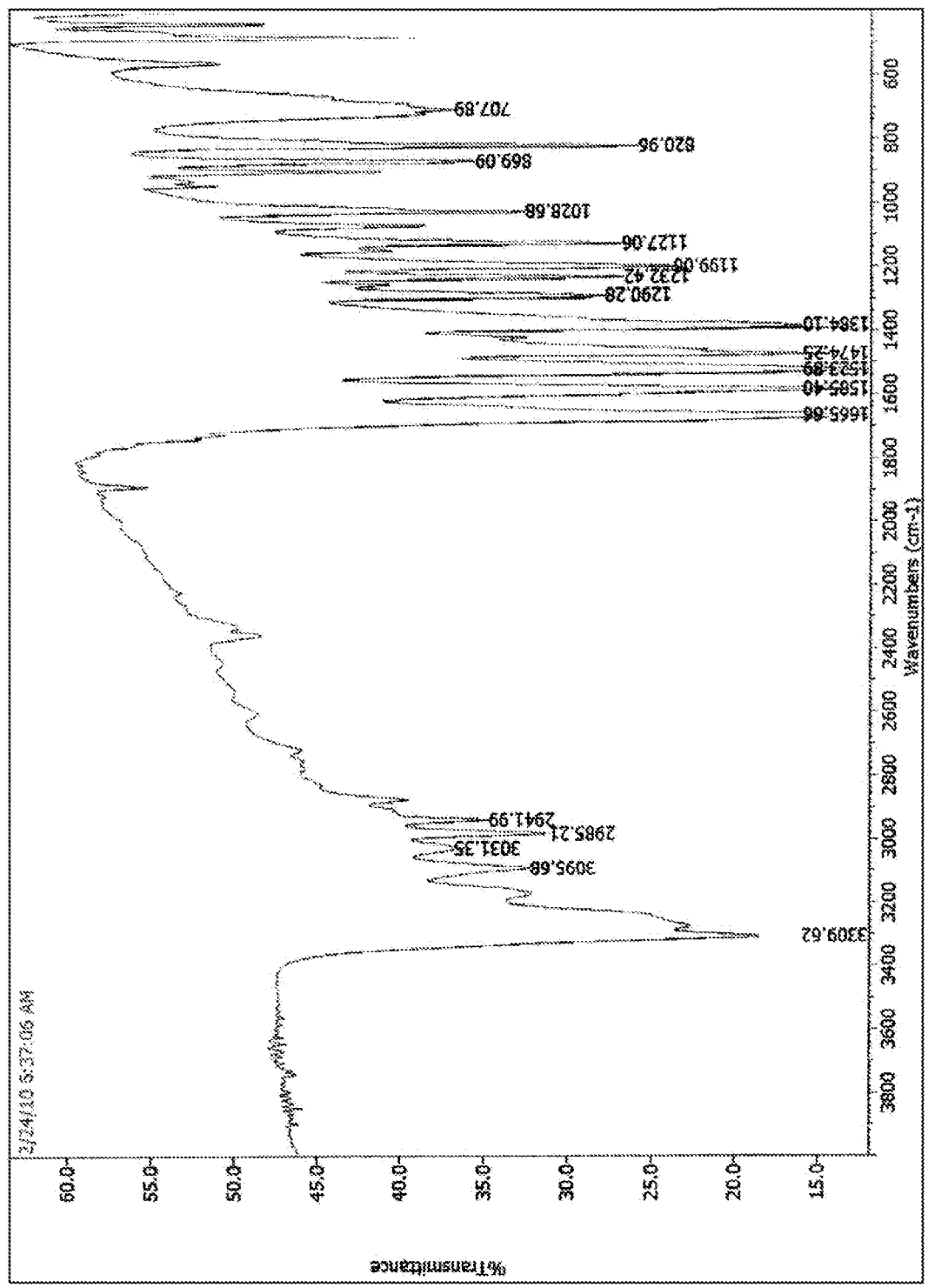
FIG. 4 illustrates an Infrared Spectrum of Propanil.
Figure 5:
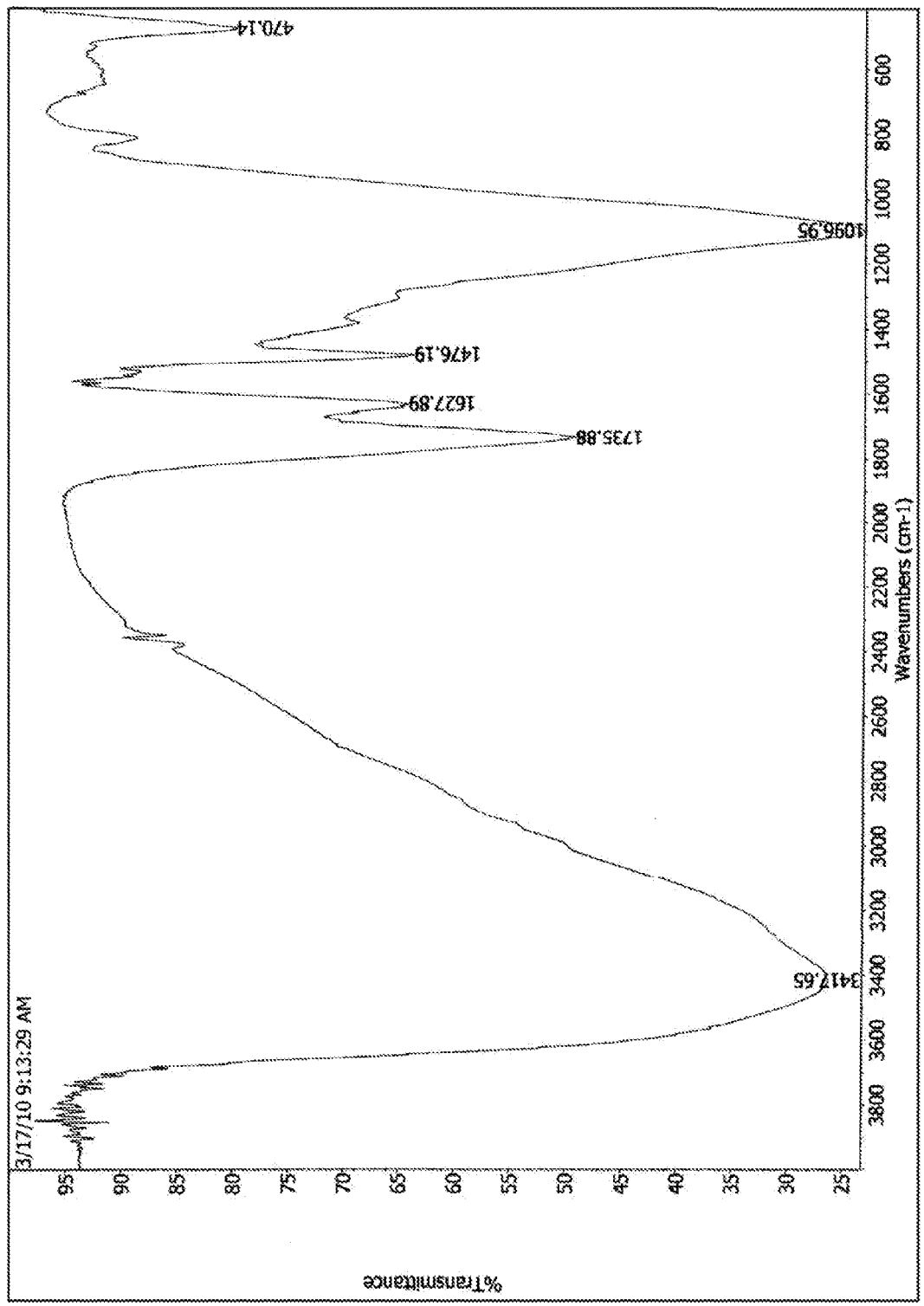
FIG. 5 illustrates an Infrared Spectrum of Propanil-functionalized Polyhydroxylated Fullerene.

Preparation of an Aromatic-Functionalized Polyhydroxylated Fullerene 0.100 g of the polyhydroxylated fullerene produced from Example 2 was reacted with 0.250 g of propanil (IUPAC name: 3,4-dichloropropionaniline), which is an aromatic compound having the chemical formula $C_9H_9C_{12}NO$, and 3.5 ml of boron trifluoride, in the form of boron trifluoride etherate (48% $BF_3$ by mass), as a Lewis acid catalyst. The mixture of fullerene and propanil was stirred continuously at a temperature in the range from about 50° C. to about 65° C. for a period of about four days to about five days. Once allowed to cool, 10 ml of ether was added to the reaction mixture and cooled in a freezer at −20° C., forming a solid. Then the reaction mixture was ultracentrifuged and the solid was isolated and then placed in a desiccator. Using a combination of elemental analysis and infrared spectroscopy, it was determined that the resulting product, a propanil-functionalized polyhydroxylated fullerene, had a formula of $C_{60}(C_6H_3C_{12}-NHCOC_2H_5)y(OH)x$ wherein y is in the range from about 1 to about 2, and x is in the range from about 24 to about 44. Elemental analysis yielded the following results: % C 41.86, % H 2.84, % N 0.59, % Cl 3.9. FIG. 4 illustrates the infrared spectrum of propanil $C_9H_9C_{12}NO$. FIG. 5 illustrates the infrared spectrum of propanil-functionalized polyhydroxylated fullerene having the formula: $C_{60}(C_6H_3Cl_2-NHCOC_2H_5)_y(OH)_x$ wherein y is in the range from about 1 to about 2, and x is in the range from about 24 to about 44.

Example 4

Figure 6:
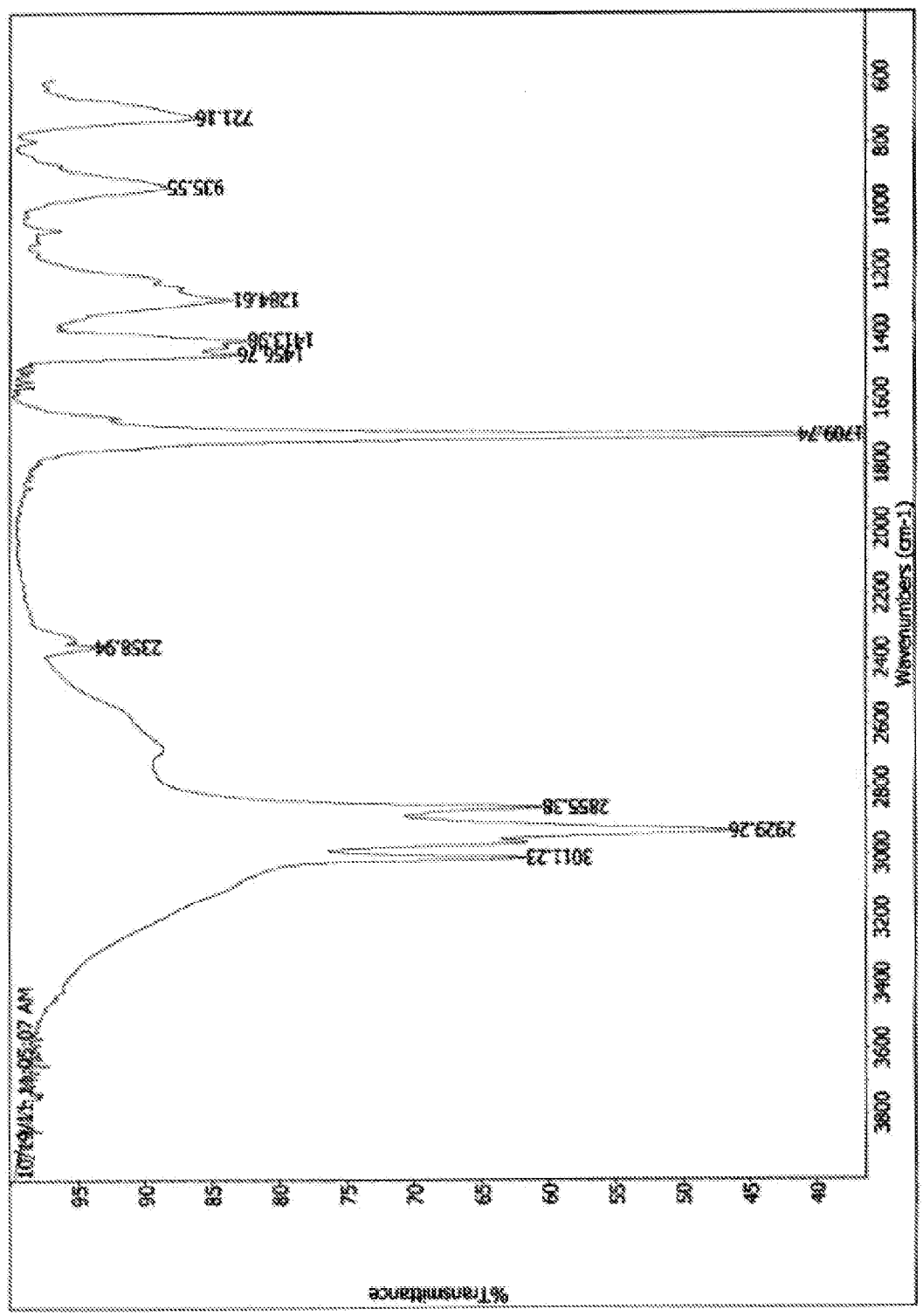
FIG. 6 illustrates an Infrared Spectrum of α-Linolenic Acid.
Figure 7:
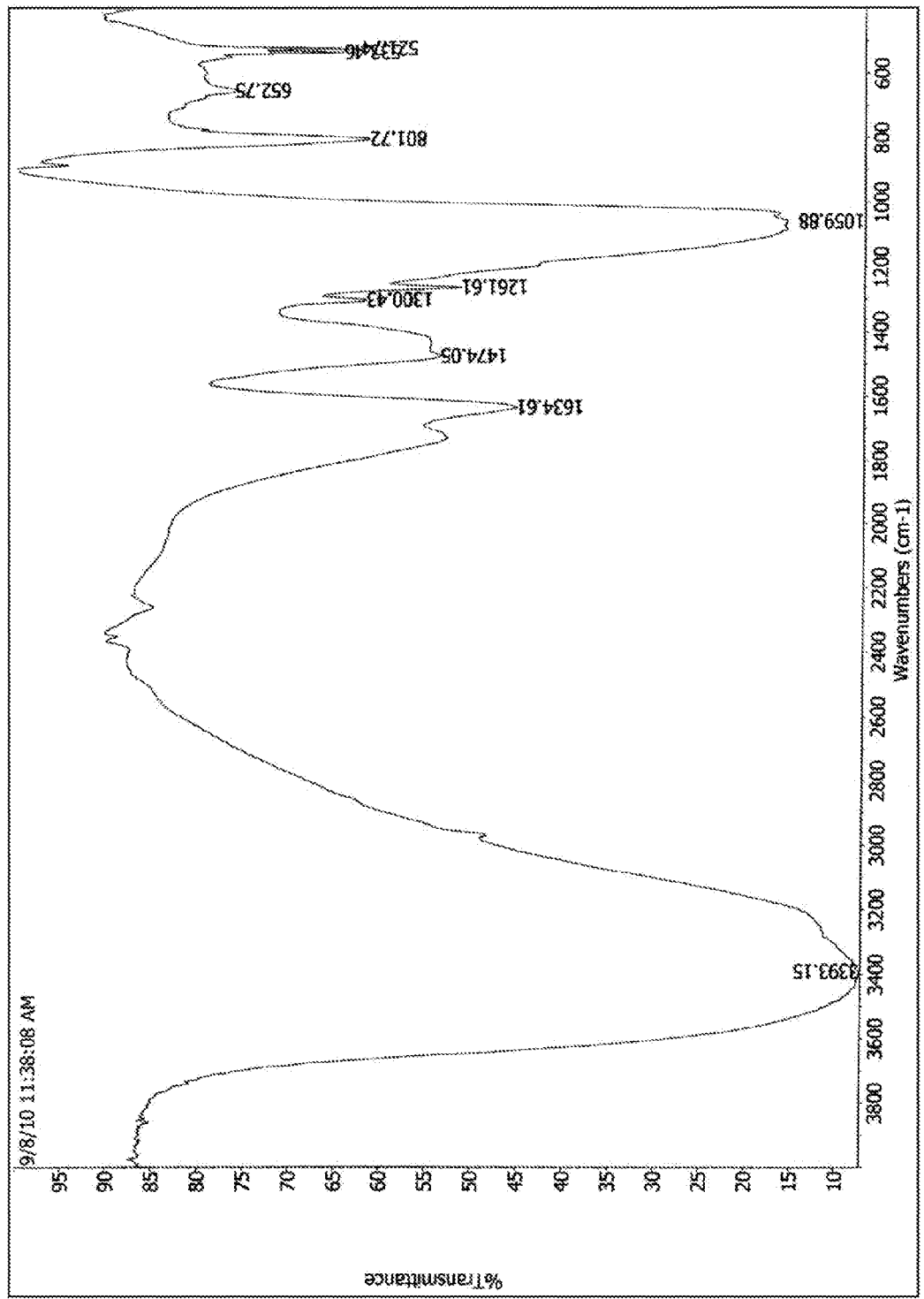
FIG. 7 illustrates an Infrared Spectrum of α-Linolenic Acid Ester-functionalized Polyhydroxylated Fullerene.

Preparation of a Fatty Acid Ester-Functionalized Polyhydroxylated Fullerene Using α-Linolenic Acid as a Fatty Acid 0.100 g of α-linolenic acid having the chemical formula $C_{18}H_{30}O_2$, an omega-3 fatty acid, was combined with an amount in the range from about 0.030 g to about 0.050 g of the polyhydroxylated fullerene produced from Example 2 and reacted with boron trifluoride as a catalyst, in the form of 4.0 ml of boron trifluoride etherate (48% $BF_3$ by mass). The mixture of α-linolenic acid and polyhydroxylated fullerene was flushed with nitrogen, sealed, and heated with constant stirring at a temperature in the range from about 50° C. to about 65° C. The reaction mixture became a homogeneous suspension. The reaction mixture was then cooled. 10 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, α-linoleic acid ester-functionalized polyhydroxylated fullerene, had a formula of $C_{60}(C_{18}H_{29}O_2)_a(OH)_b$ wherein a is in the range from about 1 to about 2 and wherein b is in the range from about 24 to about 40. Elemental analysis yielded the following results: % C 58.97% H 2.15% O 35.9. FIG. 6 illustrates the infrared spectrum of α-linolenic acid $C_{18}H_{30}O_2$. FIG. 7 illustrates the infrared spectrum of a linolenic acid ester-functionalized polyhydroxylated fullerene $C_{60}(C_{18}H_{29}O_2)_a(OH)_b$ wherein a is in the range from about 1 to about 2 and wherein b is in the range from about 24 to about 40.

Example 5

Figure 8:
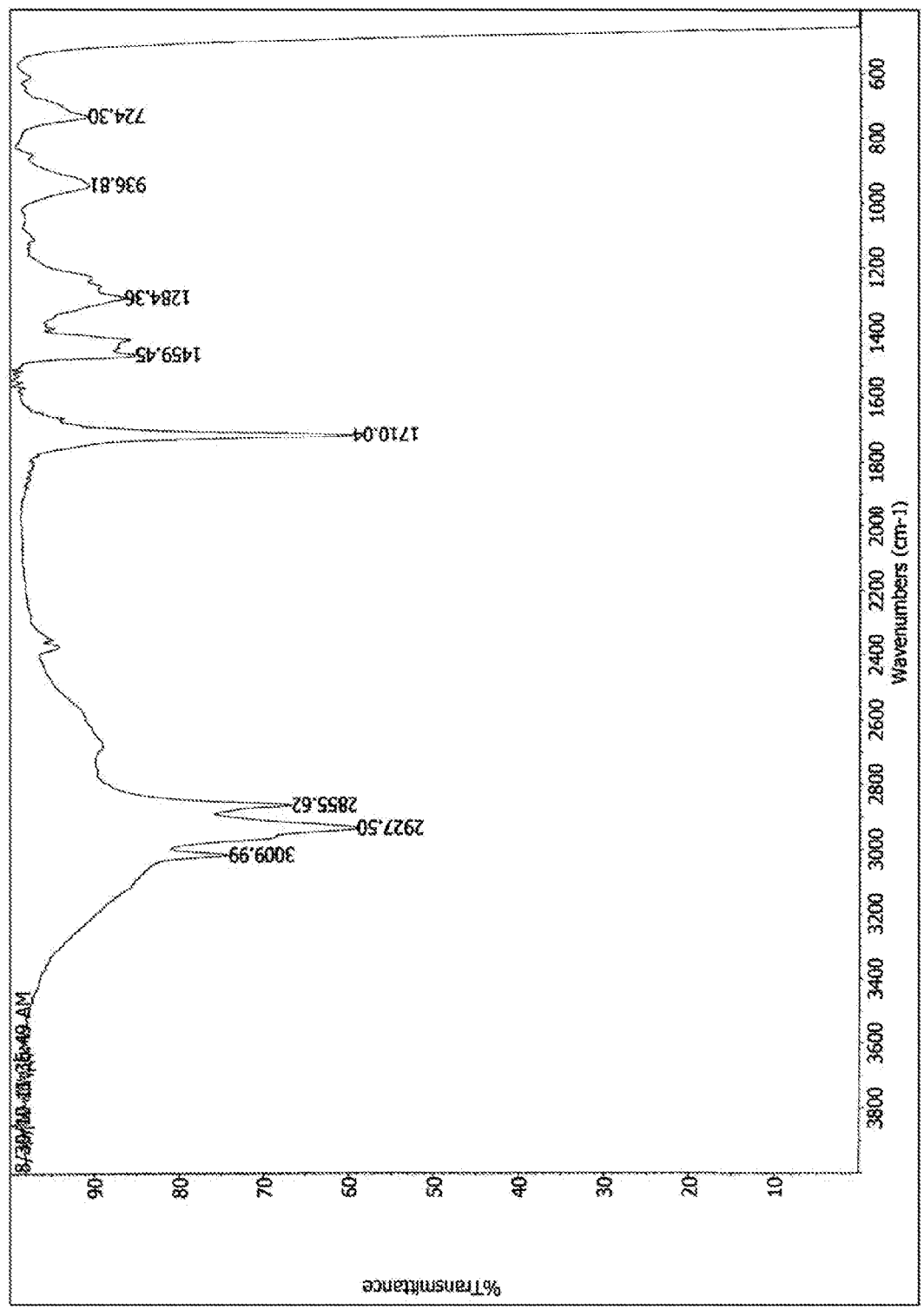
FIG. 8 illustrates an Infrared Spectrum of Linoleic Acid.
Figure 9:
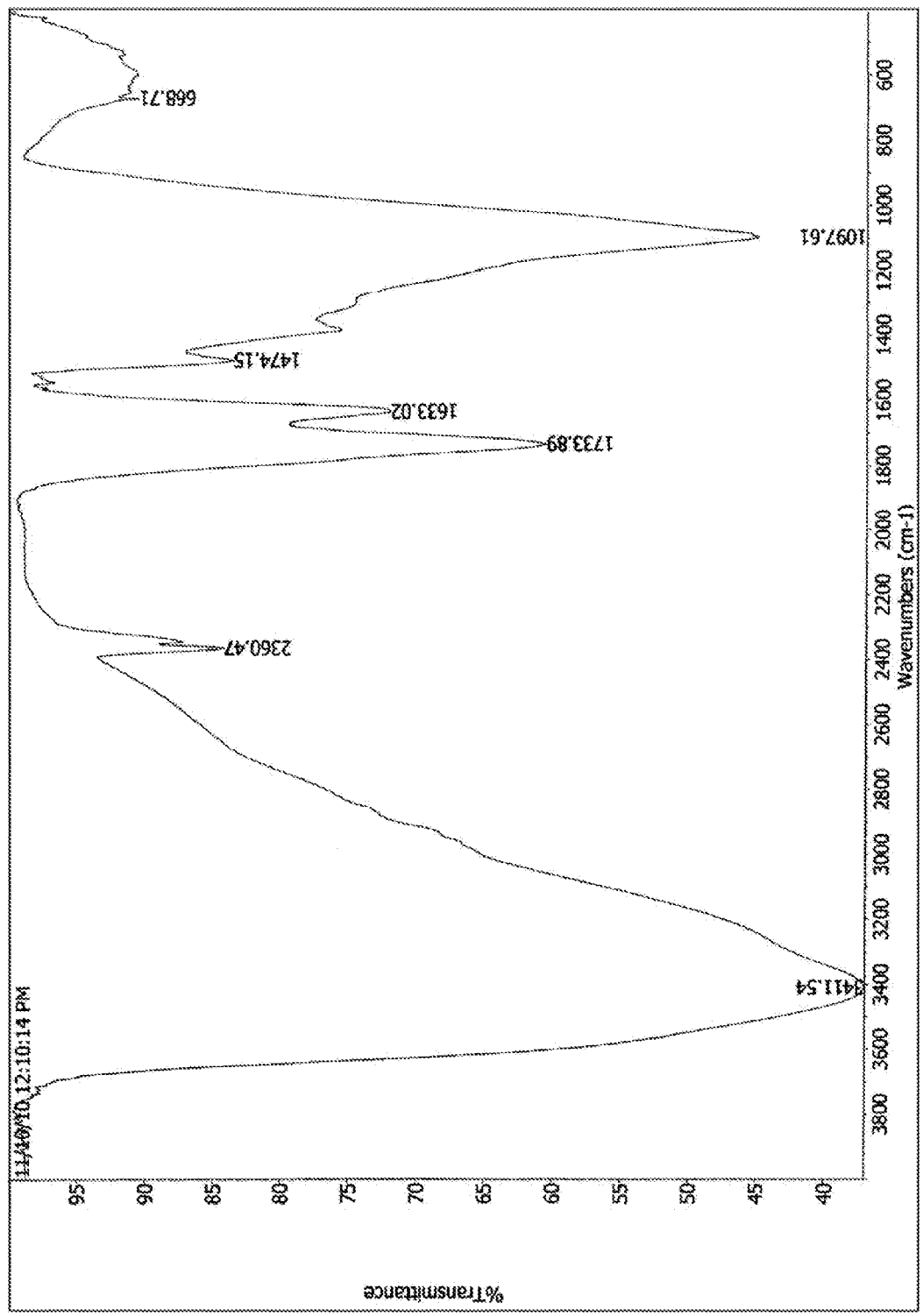
FIG. 9 illustrates an Infrared Spectrum of Linoleic Acid Ester-functionalized Polyhydroxylated Fullerene.

Preparation of a Fatty Acid Ester-Functionalized Polyhydroxylated Fullerene Using Linoleic Acid as a Fatty Acid 0.100 g of linoleic acid, which is an omega-6 fatty acid having the chemical formula $C_{18}H_{32}O_2$, was reacted with an amount from about 0.030 g to about 0.050 g of the polyhydroxylated fullerene produced in Example 2 and boron trifluoride, in the form of 4.0 ml of boron trifluoride etherate (48% $BF_3$ by mass). The mixture of linoleic acid and polyhydroxylated fullerene was flushed with nitrogen, sealed, and heated with constant stirring at a temperature in the range from about 50° C. to about 65° C. The reaction mixture became a homogeneous suspension. The reaction mixture was then cooled. 10 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, a linoleic acid ester-functionalized polyhydroxylated fullerene, had a formula of $C_{60}(C_{18}H_{31}O_2)_a(OH)_b$, wherein a is in the range from about 1 to about 2 and wherein b is in the range from about 24 to about 40. Elemental analysis yielded the following results: % C 55.96% H 3.31% O 37.43. FIG. 8 illustrates the infrared spectrum of linoleic acid $C_{18}H_{32}O_2$. FIG. 9 illustrates the infrared spectrum of linoleic acid ester-functionalized polyhydroxylated fullerene $C_{60}(C_{18}H_{31}O_2)_a(OH)_b$, wherein a is in the range from about 1 to about 2 and wherein b is in the range from about 24 to about 40.

Example 6

Figure 10:
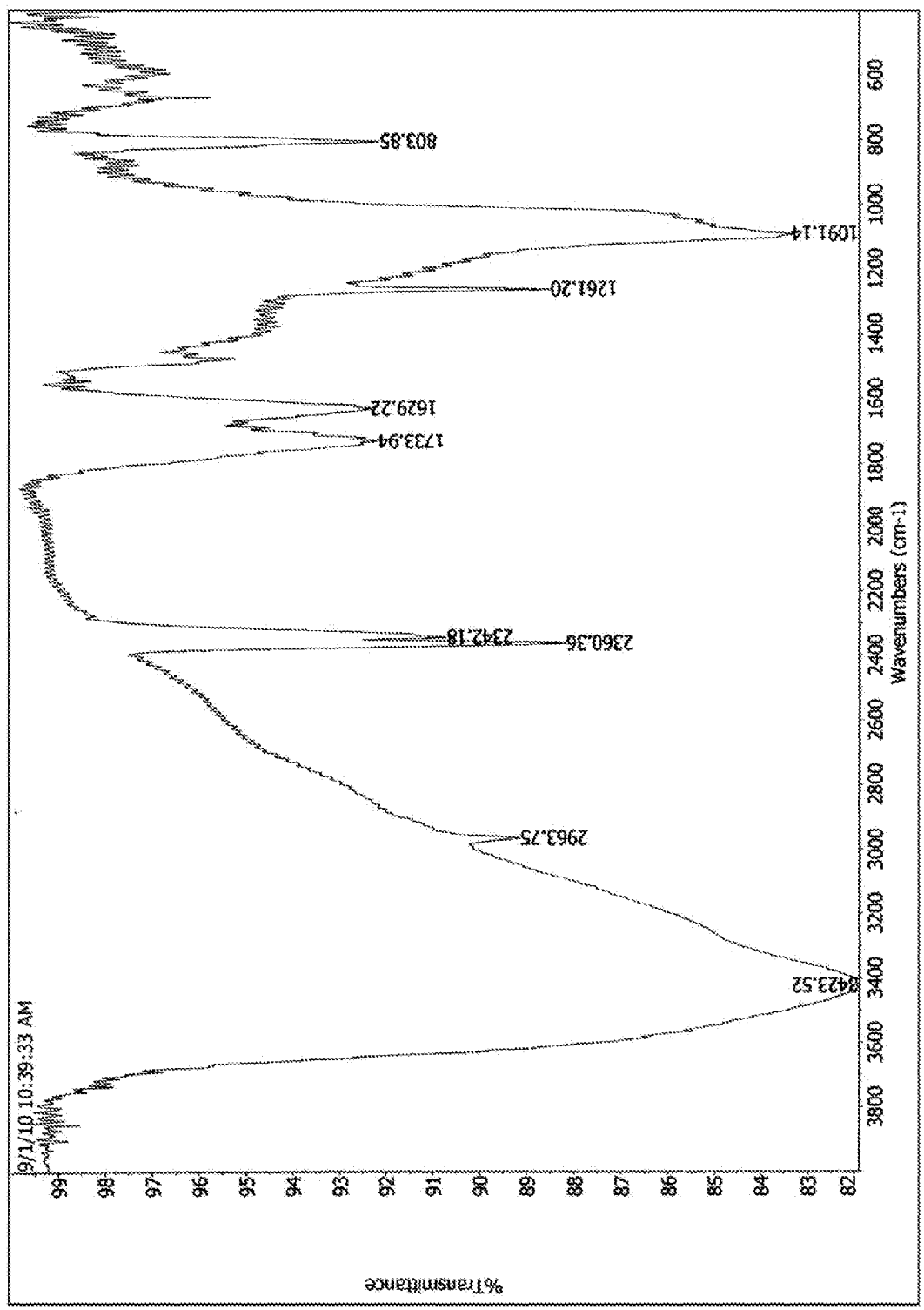
FIG. 10 illustrates an Infrared Spectrum of a Chlorine-functionalized Polyhydroxylated Fullerene.

Preparation of a Halogen-Functionalized Polyhydroxylated Fullerene 0.022 g of the polyhydroxylated fullerene produced from Example 2 and 10 ml of concentrated hydrochloric acid (HCl) were reacted together. The reaction mixture was heated at a temperature in the range from about 50° C. to about 70° C. for about two days. The product was obtained by evaporation. Using a combination of elemental analysis and infrared spectroscopy, it was determined that the resulting product, a chlorine-functionalized polyhydroxylated fullerene, had a formula of $C_{60}(X)_a(OH)_b$ wherein X is Cl, a is about 1, and wherein b is in the range from about 24 to about 44. Elemental analysis yielded the following results: % C 45.14, % H 2.59, % O 49.11, % Cl 1.70. FIG. 10 illustrates the infrared spectrum of a chlorine-functionalized polyhydroxylated fullerene.

Example 7

Figure 11:
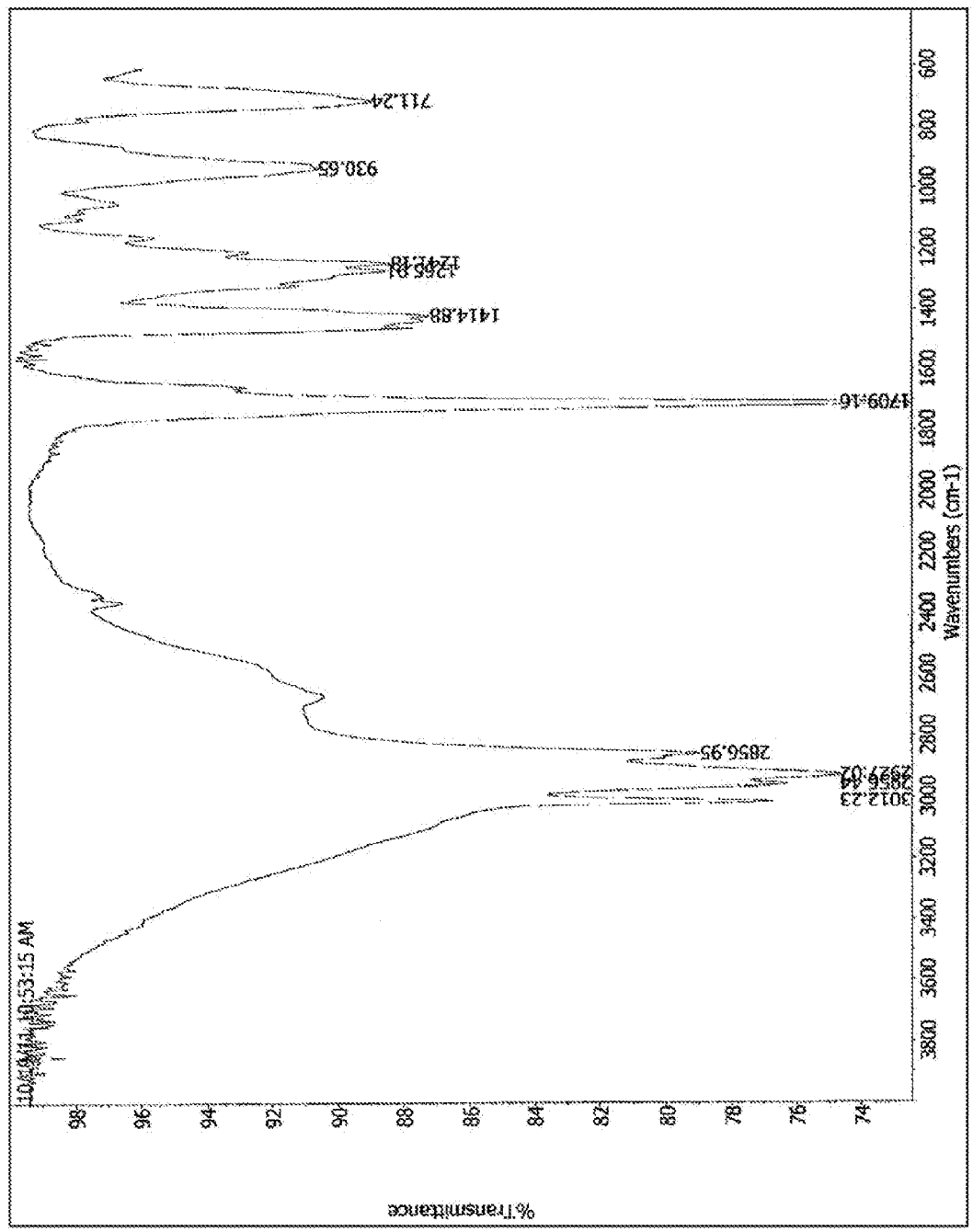
FIG. 11 illustrates an Infrared Spectrum of Arachidonic Acid.
Figure 12:
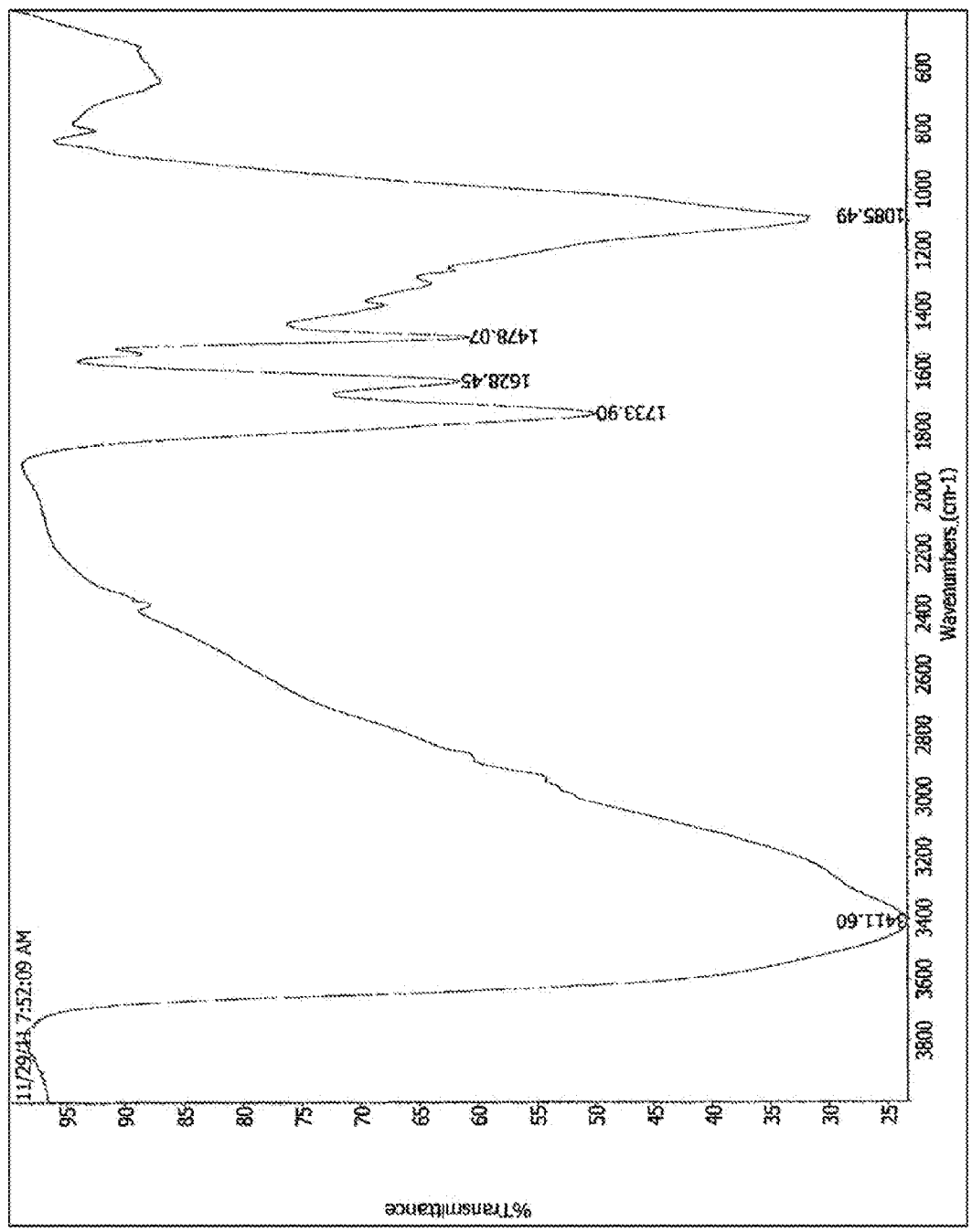
FIG. 12 illustrates an Infrared Spectrum of Arachidonic Acid-functionalized Polyhydroxylated Fullerene after a 2 day reaction period.
Figure 13:
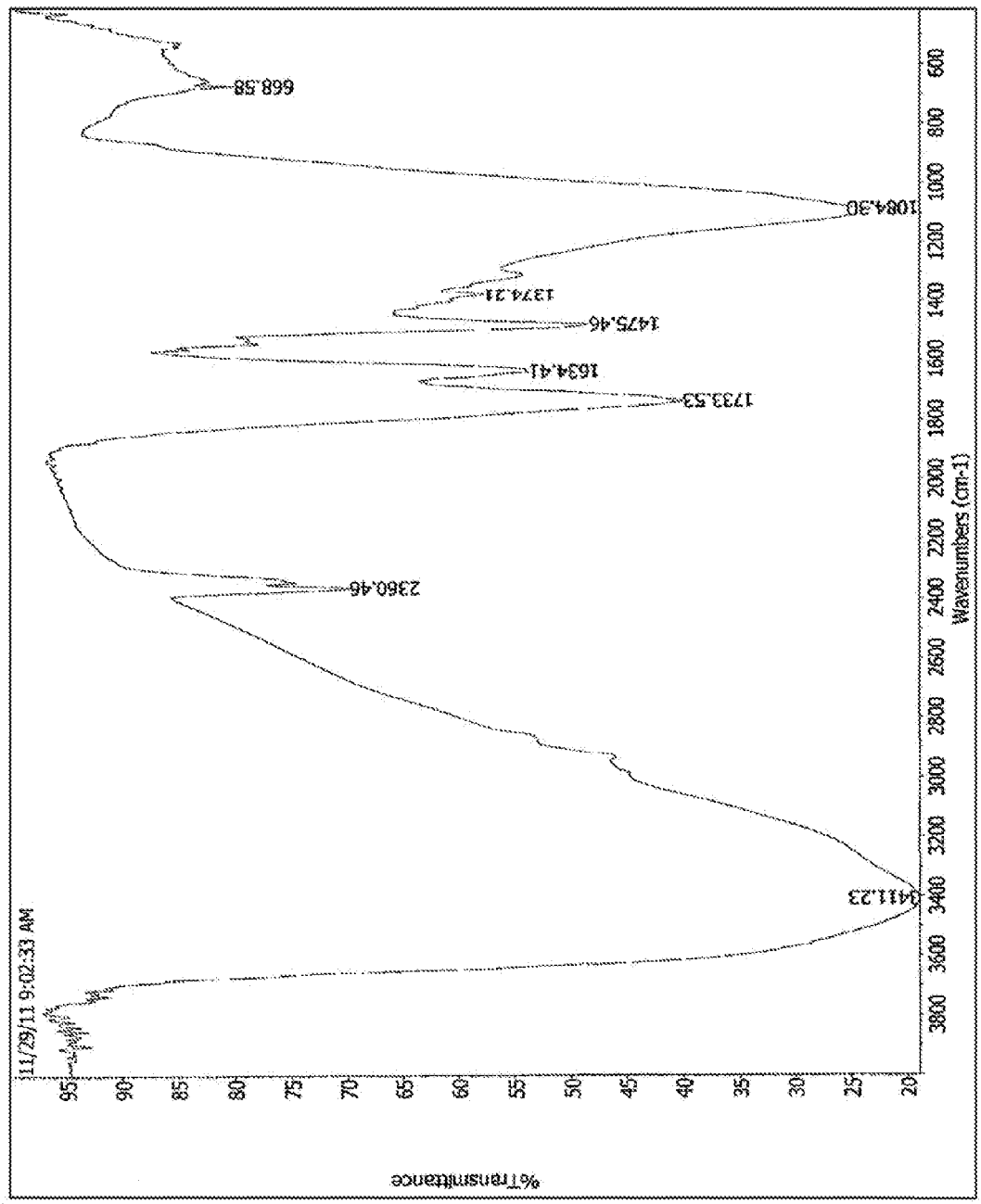
FIG. 13 illustrates an Infrared Spectrum of Arachidonic Acid-functionalized Polyhydroxylated Fullerene after a 5 day reaction period.

Preparation of an Arachidonic Acid-Functionalized Polyhydroxylated Fullerene 0.050 g of the polyhydroxylated fullerene produced from Example 2 was reacted with 0.110 g of arachidonic acid, which is an omega-6 fatty acid compound having the chemical formula $C_{20}H_{32}O_2$, and 3.8 ml of boron trifluoride, in the form of boron trifluoride etherate (48% $BF_3$ by mass). The mixture of fullerene and arachidonic acid was flushed with nitrogen, sealed, and heated with constant stirring at a temperature in the range from about 50° C. to about 65° C. for a period of about two days to about five days. The reaction mixture became a homogeneous suspension. The reaction mixture was then cooled. 25 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, an arachidonic acid-functionalized polyhydroxylated fullerene, had a formula of $C_{60}(OH)_x(C_{20}H_{32}O_2)_y$, wherein y is about 1, and wherein x is in the range from about 24 to about 44. With a 2 day reaction period, elemental analysis yielded the following results: % C 49.66, % H 3.38. With a 5 day reaction period, elemental analysis yielded the following results: % C 50.53, % H 3.43. FIG. 11 illustrates the infrared spectrum of arachidonic acid $C_{20}H_{32}O_2$. FIG. 12 illustrates the infrared spectrum of arachidonic acid-functionalized polyhydroxylated fullerene $C_{60}(OH)_x(C_{20}H_{32}O_2)_y$, that was produced from reacting the mixture of fullerene and arachidonic acid for 2 days, wherein y is about 1, and wherein x is in the range from about 24 to about 44. FIG. 13 illustrates the infrared spectrum of arachidonic acid-functionalized polyhydroxylated fullerene $C_{60}(OH)_x(C_{20}H_{32}O_2)_y$, that was produced from reacting the mixture of fullerene and arachidonic acid for 5 days, wherein y is about 1, and wherein x is in the range from about 24 to about 44.

Example 8

Figure 14:
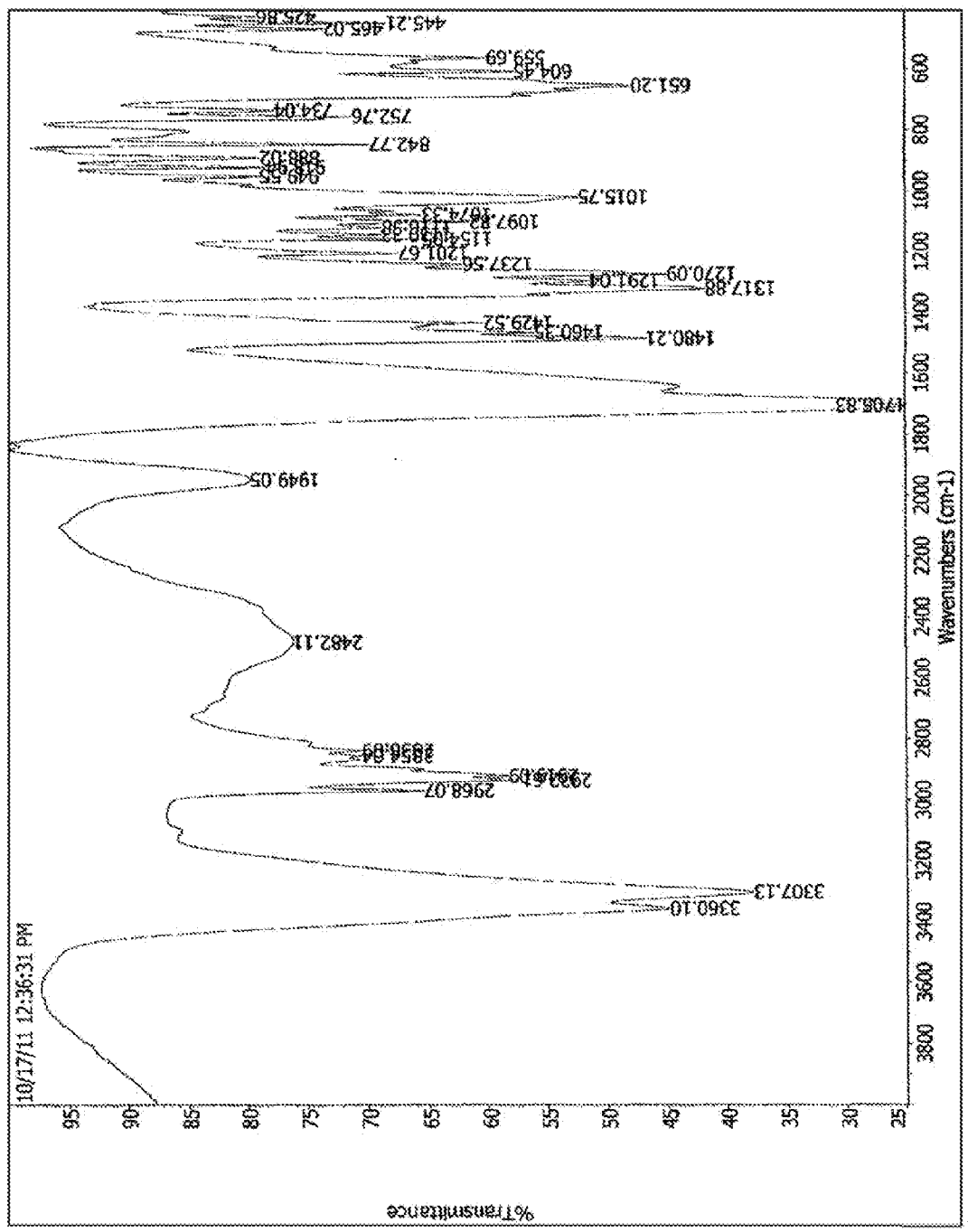
FIG. 14 illustrates an Infrared Spectrum of Biotin.
Figure 15:
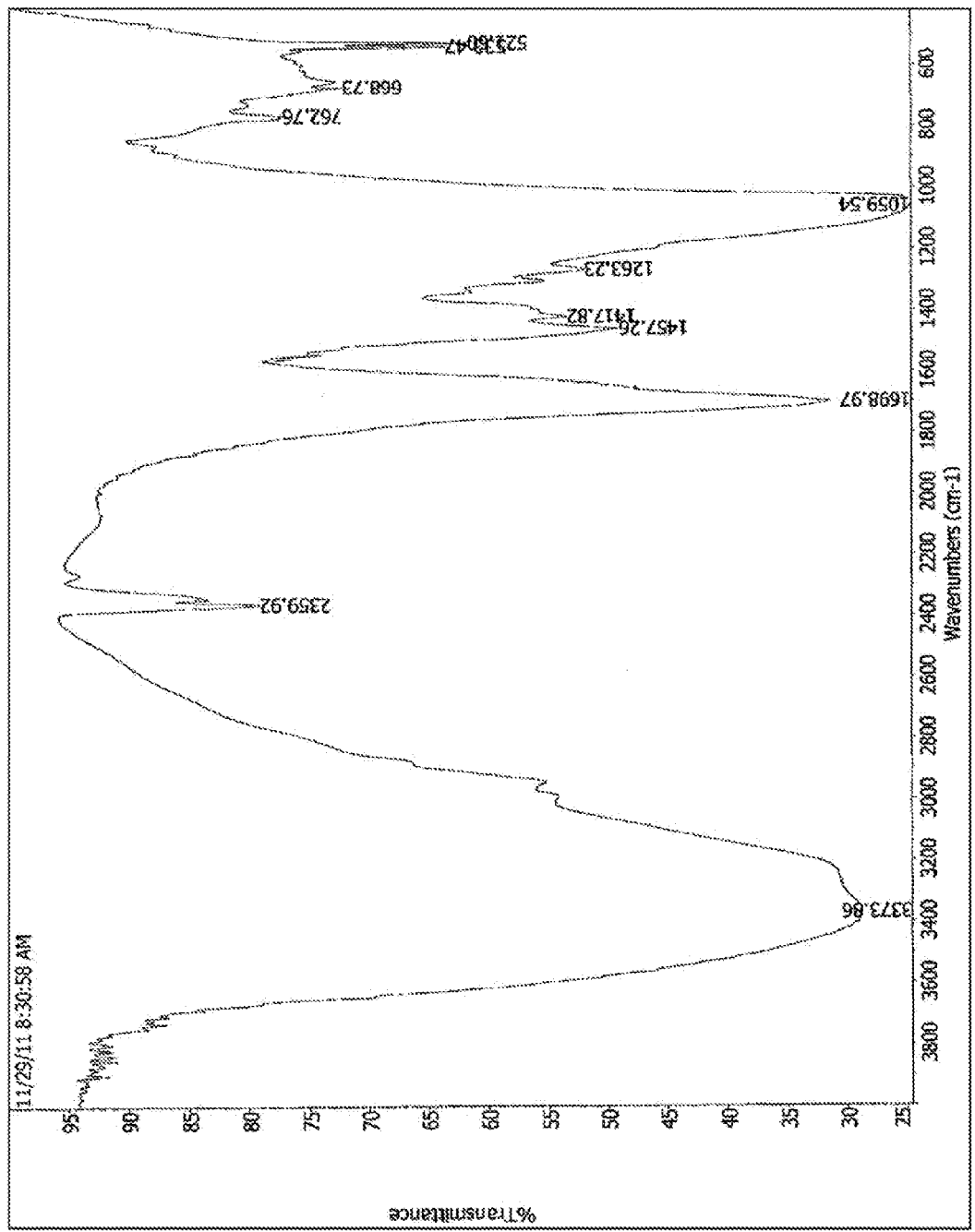
FIG. 15 illustrates an Infrared Spectrum of Biotin-functionalized Polyhydroxylated Fullerene.

Preparation of a Biotin-Functionalized Polyhydroxylated Fullerene 0.050 g of the polyhydroxylated fullerene produced from Example 2 was reacted with 0.100 g of biotin, which is a vitamin having the chemical formula $C_{10}H_{16}N_2O_3S$, and 4.2 ml of boron trifluoride, in the form of boron trifluoride etherate (48% $BF_3$ by mass). The mixture of fullerene and biotin was flushed with nitrogen, sealed, and heated with constant stirring at a temperature in the range from about 50° C. to about 65° C. for a period of about five days. The reaction mixture became a homogeneous suspension. The reaction mixture was then cooled. 25 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, a biotin-functionalized polyhydroxylated fullerene, had a formula of $C_{60}(OH)_x(C_{10}H_{16}N_2O_3S)_y$, wherein y is about 3.5, and wherein x is in the range from about 24 to about 41. Elemental analysis yielded the following results: % C 37.82, % H 5.72, % N 4.3, % S 5.098. FIG. 14 illustrates the infrared spectrum of biotin $C_{10}H_{16}N_2O_3S$. FIG. 15 illustrates the infrared spectrum of biotin-functionalized polyhydroxylated fullerene $C_{60}(OH)_x(C_{10}H_{16}N_2O_3S)_y$, wherein y is about 3.5 and wherein x is in the range from about 24 to about 41.

Example 9

Figure 16:
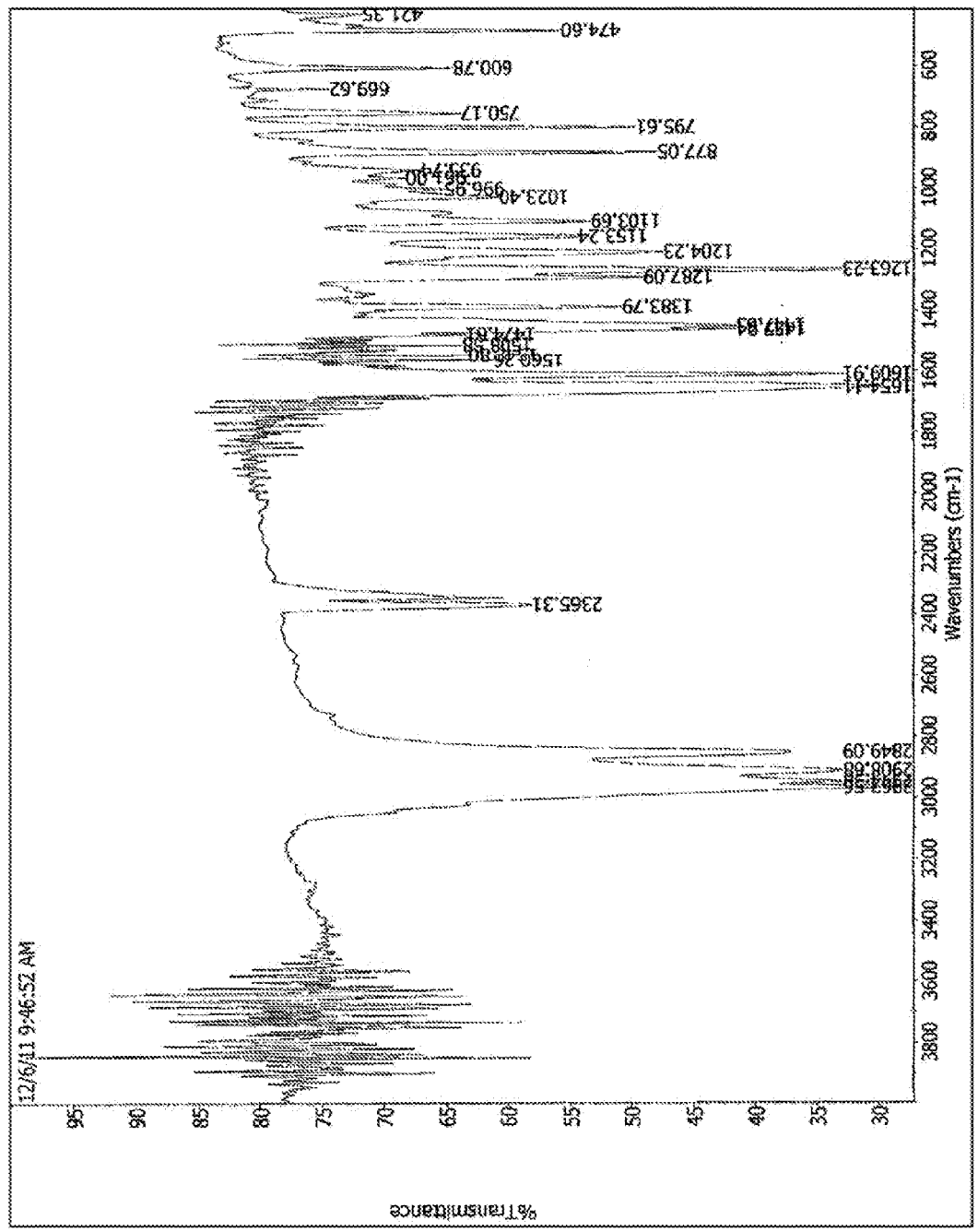
FIG. 16 illustrates an Infrared Spectrum of Coenzyme Q$_{10}$.
Figure 17:
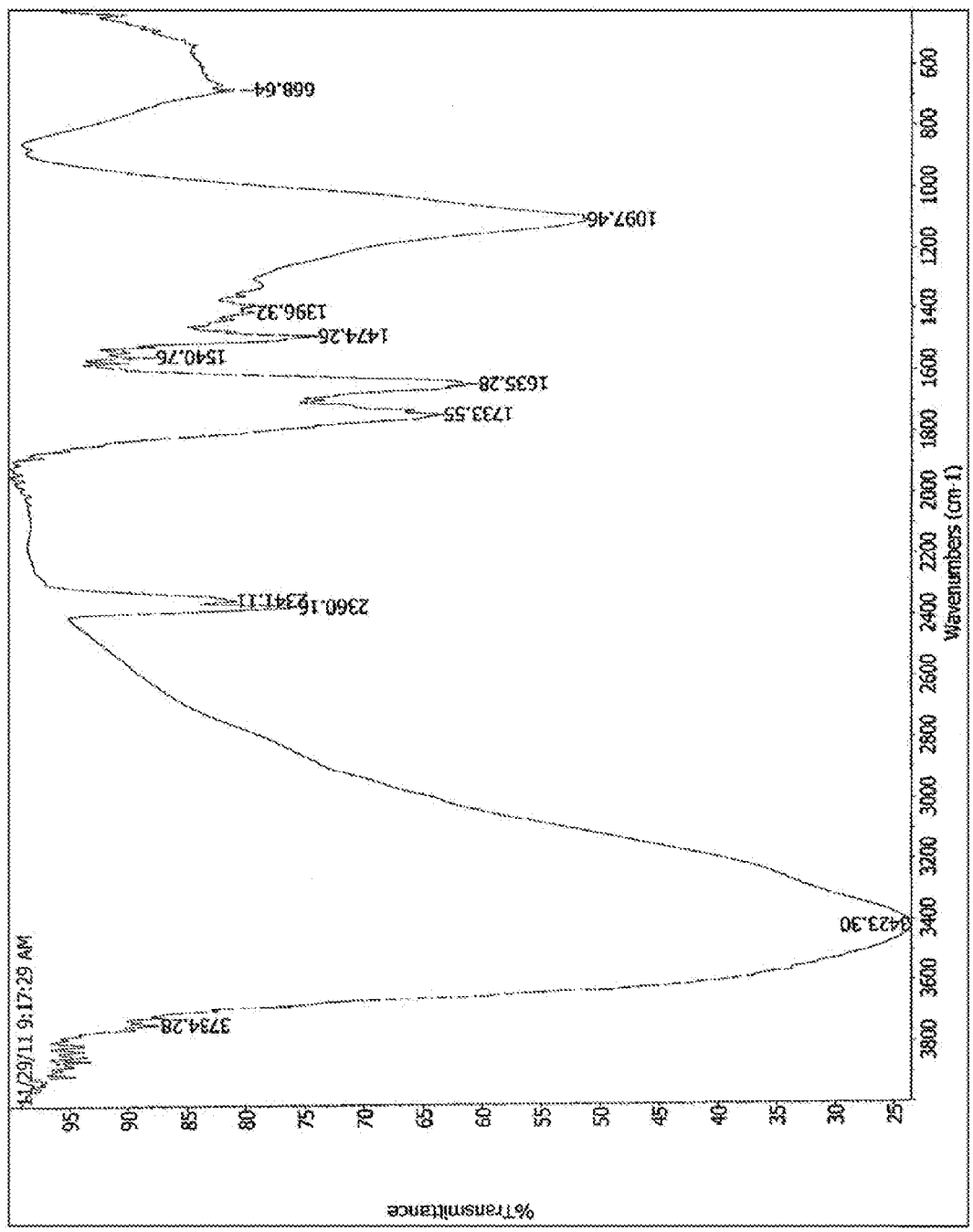
FIG. 17 illustrates an Infrared Spectrum of Coenzyme Q$_{10}$-functionalized Polyhydroxylated Fullerene.

Preparation of a Coenzyme $Q_{10}$-Functionalized Polyhydroxylated Fullerene 0.053 g of the polyhydroxylated fullerene produced from Example 2 was reacted with 0.098 g of coenzyme $Q_{10}$, which is a vitamin having the chemical formula $C_{59}H_{90}O_4$, and 4.2 ml of boron trifluoride, in the form of boron trifluoride etherate (48% $BF_3$ by mass). The mixture of fullerene and coenzyme $Q_{10}$ was flushed with nitrogen, sealed, and heated with constant stirring at a temperature in the range from about 50° C. to about 65° C. for a period of about five days. The reaction mixture became a homogeneous suspension. The reaction mixture was then cooled. 25 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, a coenzyme $Q_{10}$-functionalized polyhydroxylated fullerene, had a formula of $C_{60}(OH)_x(C_{59}H_{90}O_4)_y$, wherein y is about 1, and wherein x is in the range from about 24 to about 44. Elemental analysis yielded the following results: % C 48.28, % H 3.21. FIG. 16 illustrates the infrared spectrum of coenzyme $Q_{10}$ $C_{59}H_{90}O_4$. FIG. 17 illustrates the infrared spectrum of coenzyme Q$_{10}$-functionalized polyhydroxylated fullerene C$_{60}$(OH)$_x$(C$_{59}$H$_{90}$O$_4$)$_y$, wherein y is about 1, and wherein x is in the range from about 24 to about 44.

Example 10

Figure 18:
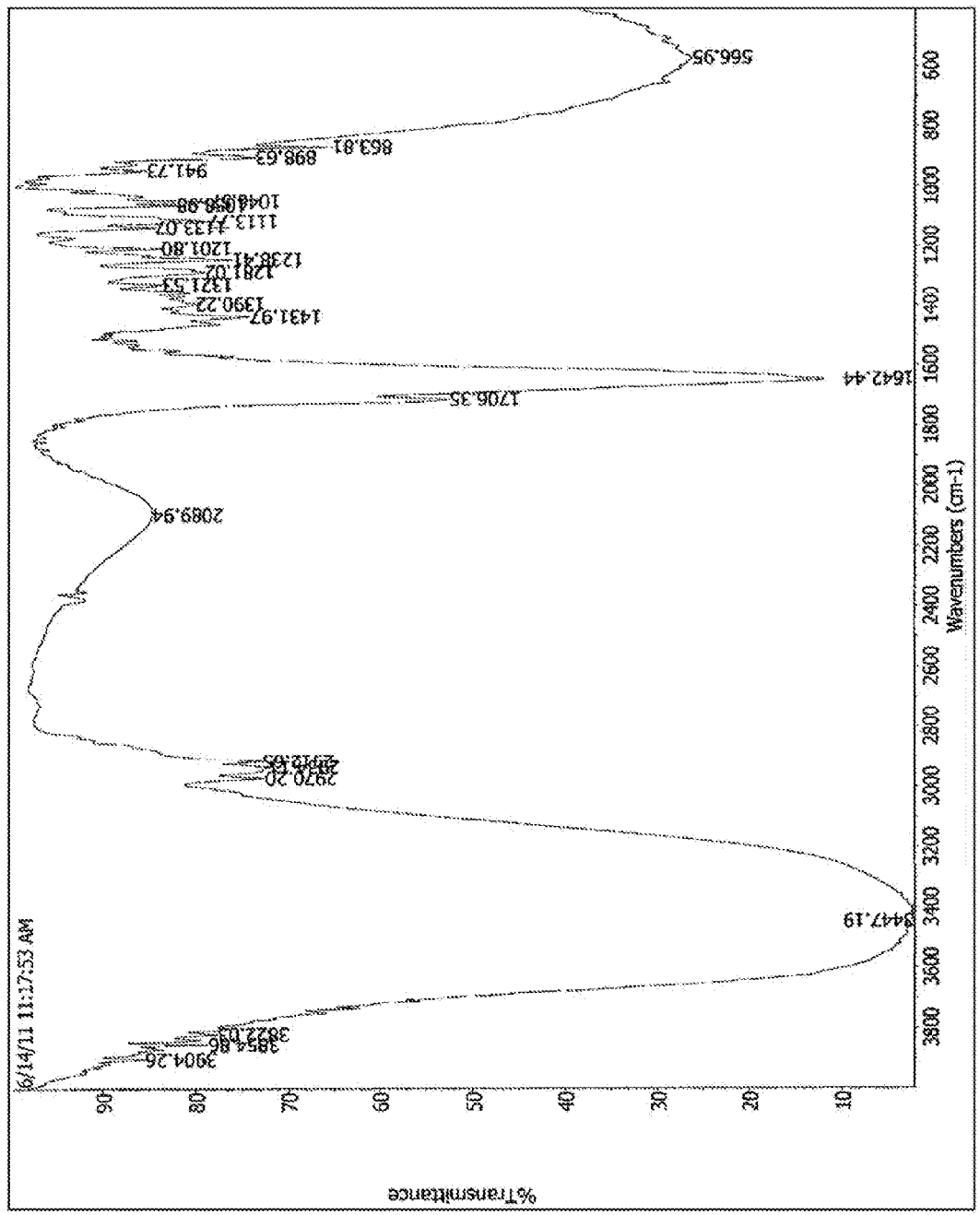
FIG. 18 illustrates an Infrared Spectrum of Hydrocortisone.
Figure 19:
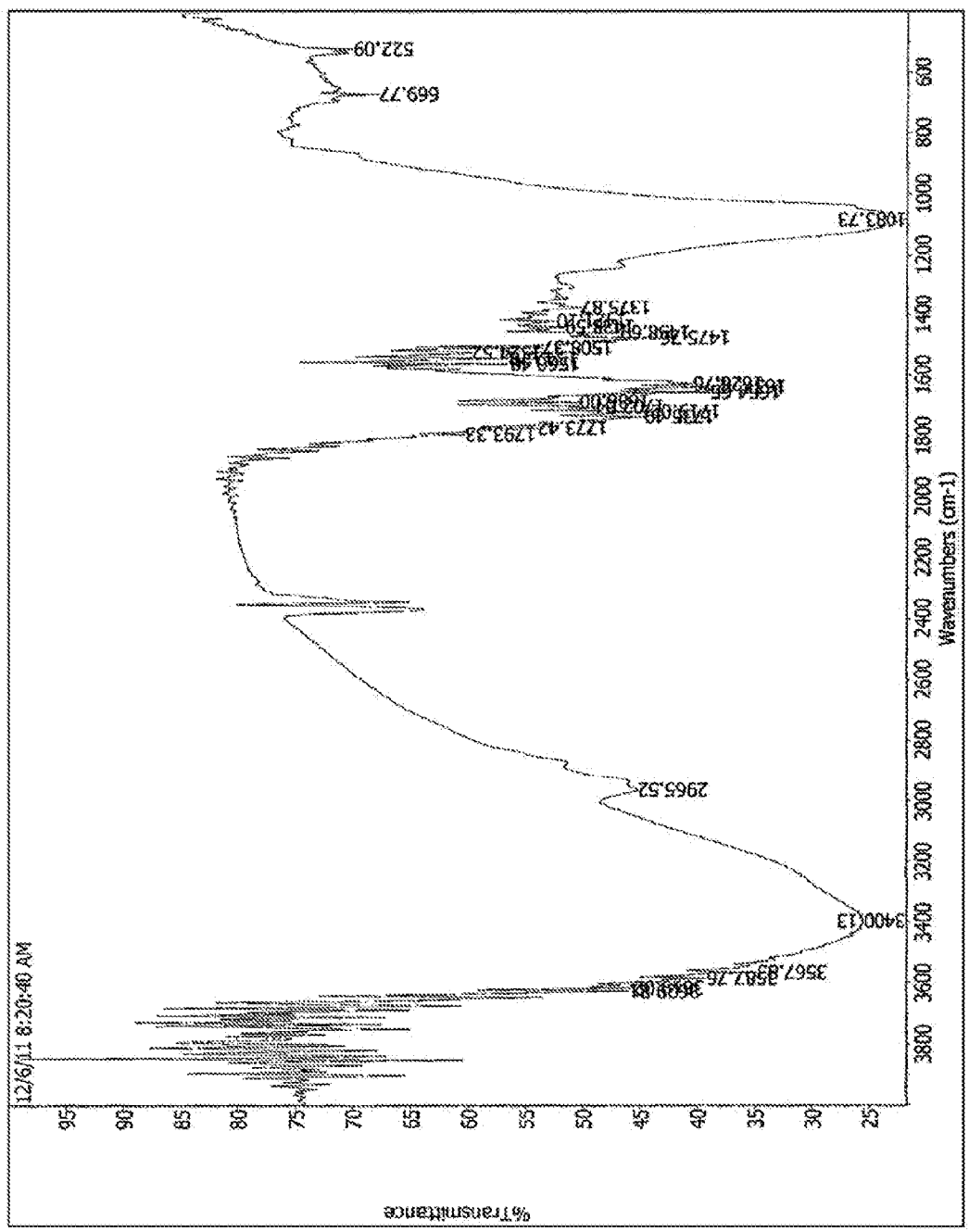
FIG. 19 illustrates an Infrared Spectrum of Hydrocortisone-functionalized Polyhydroxylated Fullerene.

Preparation of a Hydrocortisone-Functionalized Polyhydroxylated Fullerene 0.049 g of the polyhydroxylated fullerene produced from Example 2 was reacted with 0.103 g of hydrocortisone, which is a corticosteroid having the chemical formula C$_{21}$H$_{30}$O$_5$, and 4.2 ml of boron trifluoride, in the form of boron trifluoride etherate (48% BF$_3$ by mass). The mixture of fullerene and hydrocortisone was flushed with nitrogen, sealed, and heated with constant stirring at a temperature in the range from about 50° C. to about 65° C. for a period of about five days. The reaction mixture became a homogeneous suspension. The reaction mixture was then cooled. 25 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, a hydrocortisone-functionalized polyhydroxylated fullerene, had a formula of C$_{60}$(OH)$_x$(C$_{21}$H$_{30}$O$_5$)$_y$, wherein y is about 1, and wherein x is in the range from about 24 to about 44. Elemental analysis yielded the following results: % C 53.12, % H 4.17. FIG. 18 illustrates the infrared spectrum of hydrocortisone C$_{21}$H$_{30}$O$_5$. FIG. 19 illustrates the infrared spectrum of hydrocortisone-functionalized polyhydroxylated fullerene C$_{60}$(OH)$_x$(C$_{21}$H$_{30}$O$_5$)$_y$, wherein y is about 1, and wherein x is in the range from about 24 to about 44.

Example 11

Figure 20:
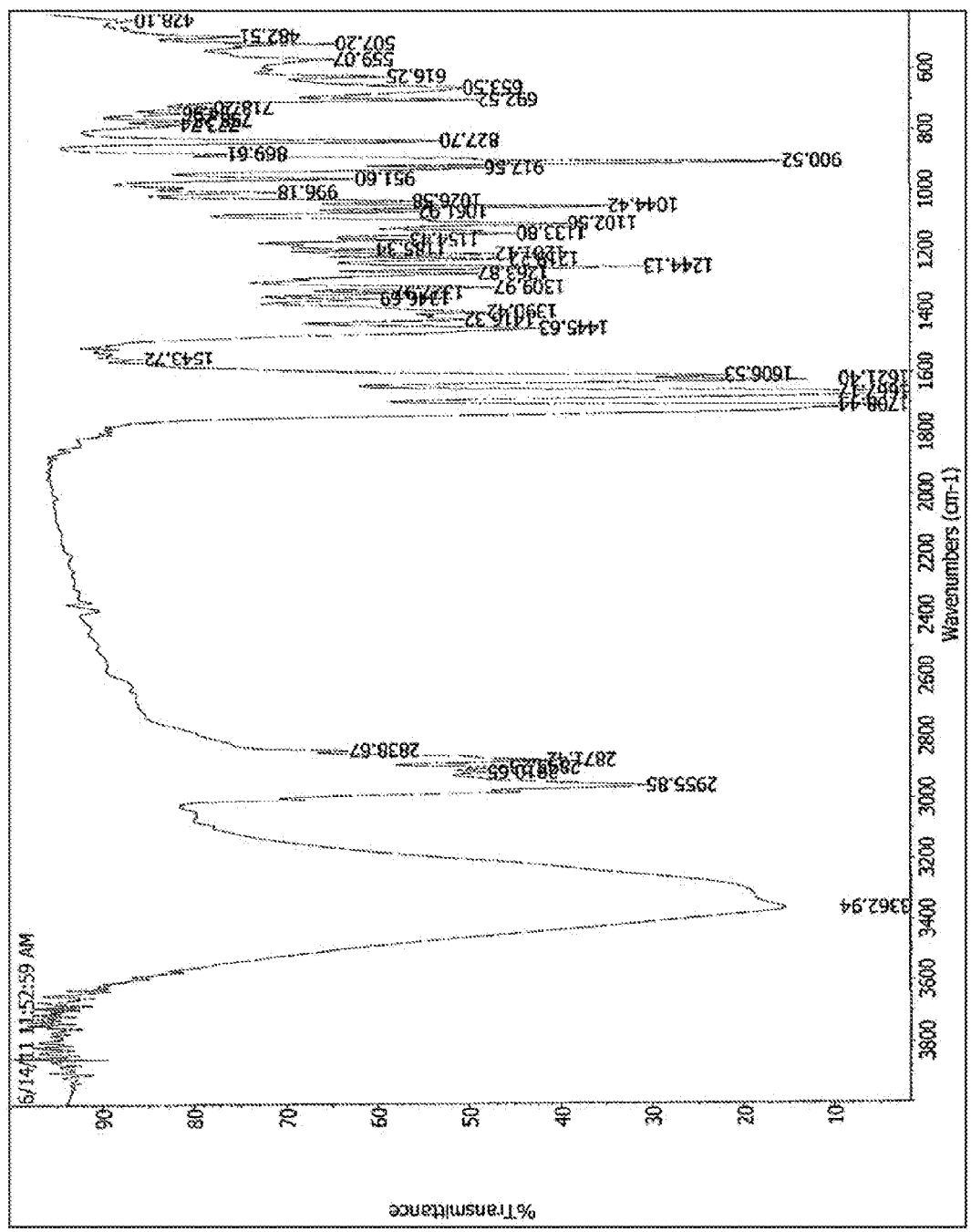
FIG. 20 illustrates an Infrared Spectrum of Prednisone.
Figure 21:
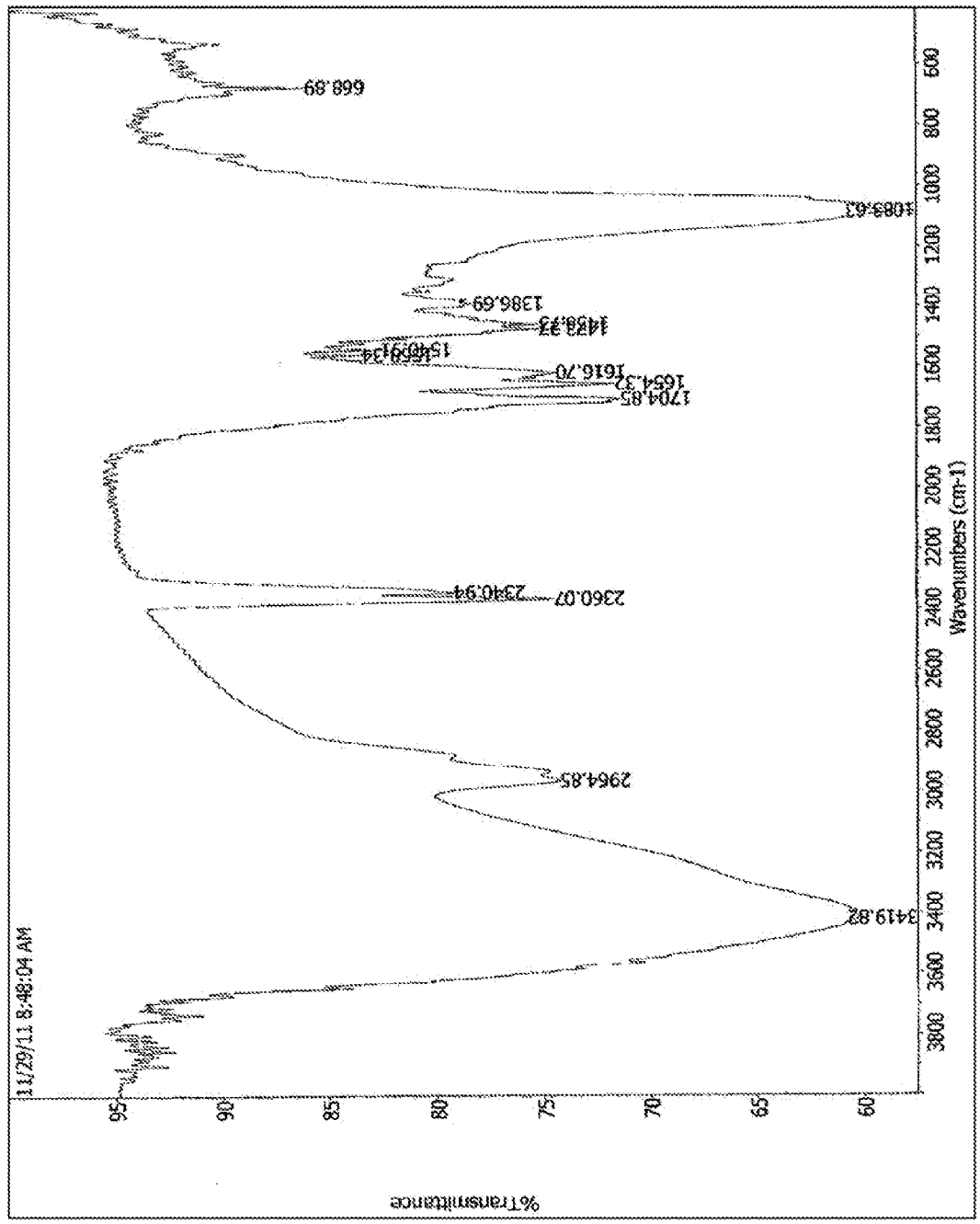
FIG. 21 illustrates an Infrared Spectrum of Prednisone-functionalized Polyhydroxylated Fullerene.

Preparation of a Prednisone-Functionalized Polyhydroxylated Fullerene 0.050 g of the polyhydroxylated fullerene produced from Example 2 was reacted with 0.102 g of prednisone, which is a corticosteroid having the chemical formula C$_{21}$H$_{26}$O$_5$, and 4.0 ml of boron trifluoride, in the form of boron trifluoride etherate (48% BF$_3$ by mass). The mixture of fullerene and prednisone was flushed with nitrogen, sealed, and heated with constant stirring at a temperature in the range from about 50° C. to about 65° C. for a period of about five days. The reaction mixture became a homogeneous suspension. The reaction mixture was then cooled. 25 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, a prednisone-functionalized polyhydroxylated fullerene, had a formula of C$_{60}$(OH)$_x$(C$_{21}$H$_{26}$O$_5$)$_y$, wherein y is about 2, and wherein x is in the range from about 24 to about 43. Elemental analysis yielded the following results: % C 59.84, % H 5.32. FIG. 20 illustrates the infrared spectrum of prednisone C$_{21}$H$_{26}$O$_5$. FIG. 21 illustrates the infrared spectrum of prednisone-functionalized polyhydroxylated fullerene C$_{60}$(OH)$_x$(C$_{21}$H$_{26}$O$_5$)$_y$, wherein y is about 2, and wherein x is in the range from about 24 to about 43.

Example 12

Figure 22:
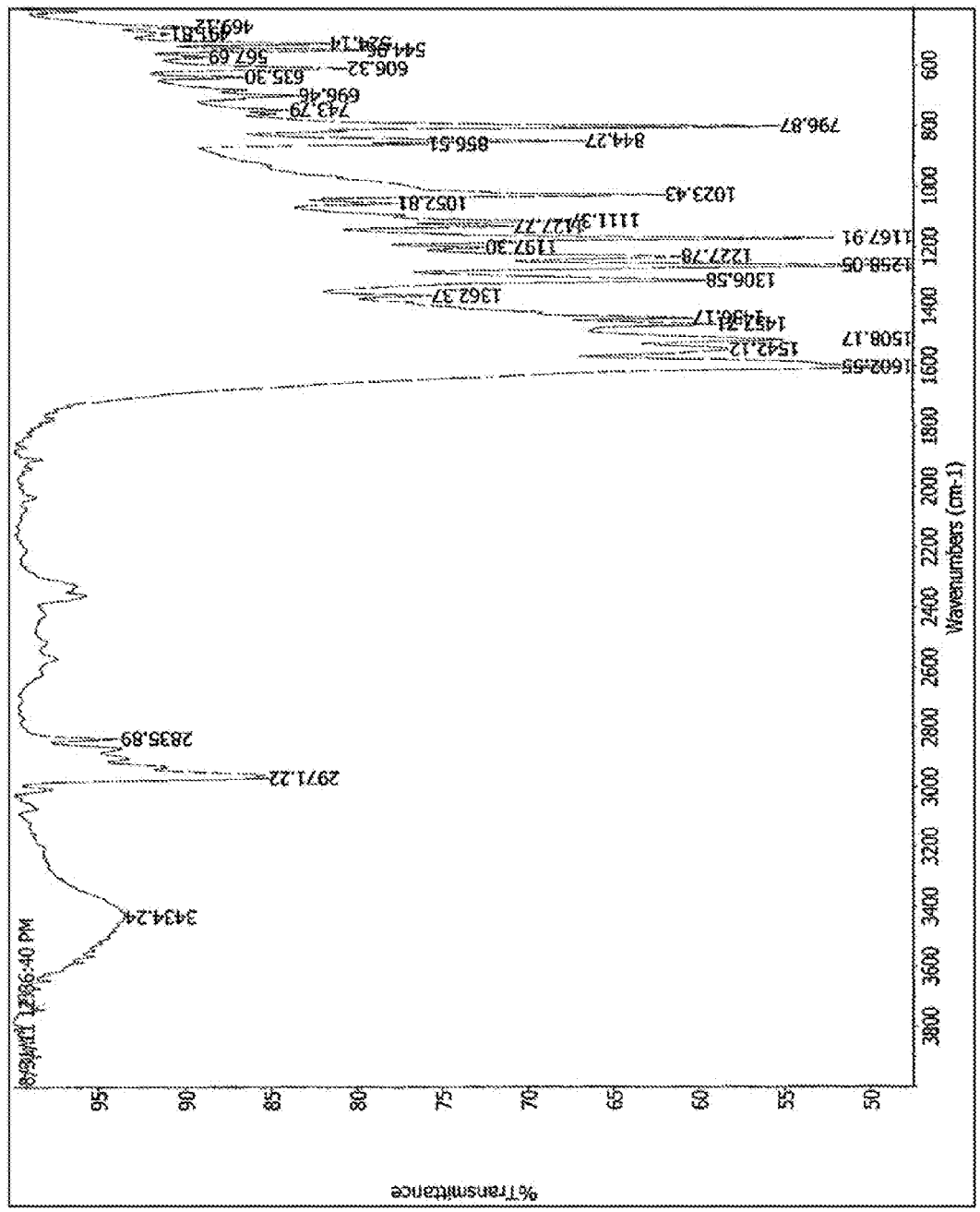
FIG. 22 illustrates an Infrared Spectrum of Avobenzone.
Figure 23:
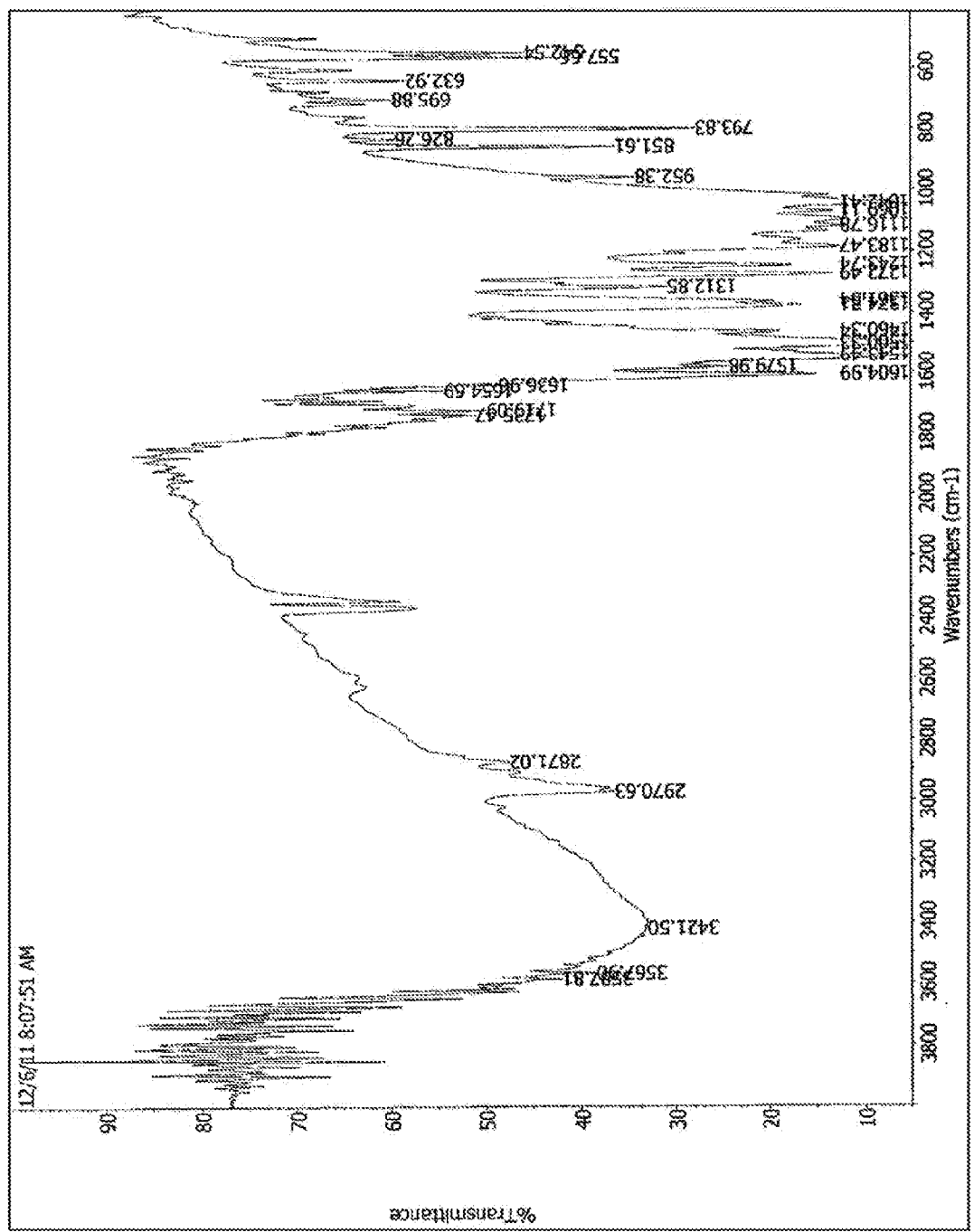
FIG. 23 illustrates an Infrared Spectrum of Avobenzone-functionalized Polyhydroxylated Fullerene.

Preparation of an Avobenzone-Functionalized Polyhydroxylated Fullerene 0.049 g of the polyhydroxylated fullerene produced from Example 2 was reacted with 0.075 g of avobenzone, which is an aromatic compound having the chemical formula C$_{20}$H$_{22}$O$_3$, and 3.8 ml of boron trifluoride, in the form of boron trifluoride etherate (48% BF$_3$ by mass). The mixture of fullerene and avobenzone was flushed with nitrogen, sealed, and heated with constant stirring at a temperature in the range from about 50° C. to about 65° C. for a period of about five days. The reaction mixture became a homogeneous suspension. The reaction mixture was then cooled. 25 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, an avobenzone-functionalized polyhydroxylated fullerene, had a formula of C$_{60}$(OH)$_x$(C$_{20}$H$_{22}$O$_3$)$_y$, wherein y is about 2, and wherein x is in the range from about 24 to about 43. Elemental analysis yielded the following results: % C 56.43, % H 4.41. FIG. 22 illustrates the infrared spectrum of avobenzone C$_{20}$H$_{22}$O$_3$. FIG. 23 illustrates the infrared spectrum of avobenzone-functionalized polyhydroxylated fullerene C$_{60}$(OH)$_x$(C$_{20}$H$_{22}$O$_3$)$_y$, wherein y is about 2, and wherein x is in the range from about 24 to about 43.

Example 13

Figure 24:
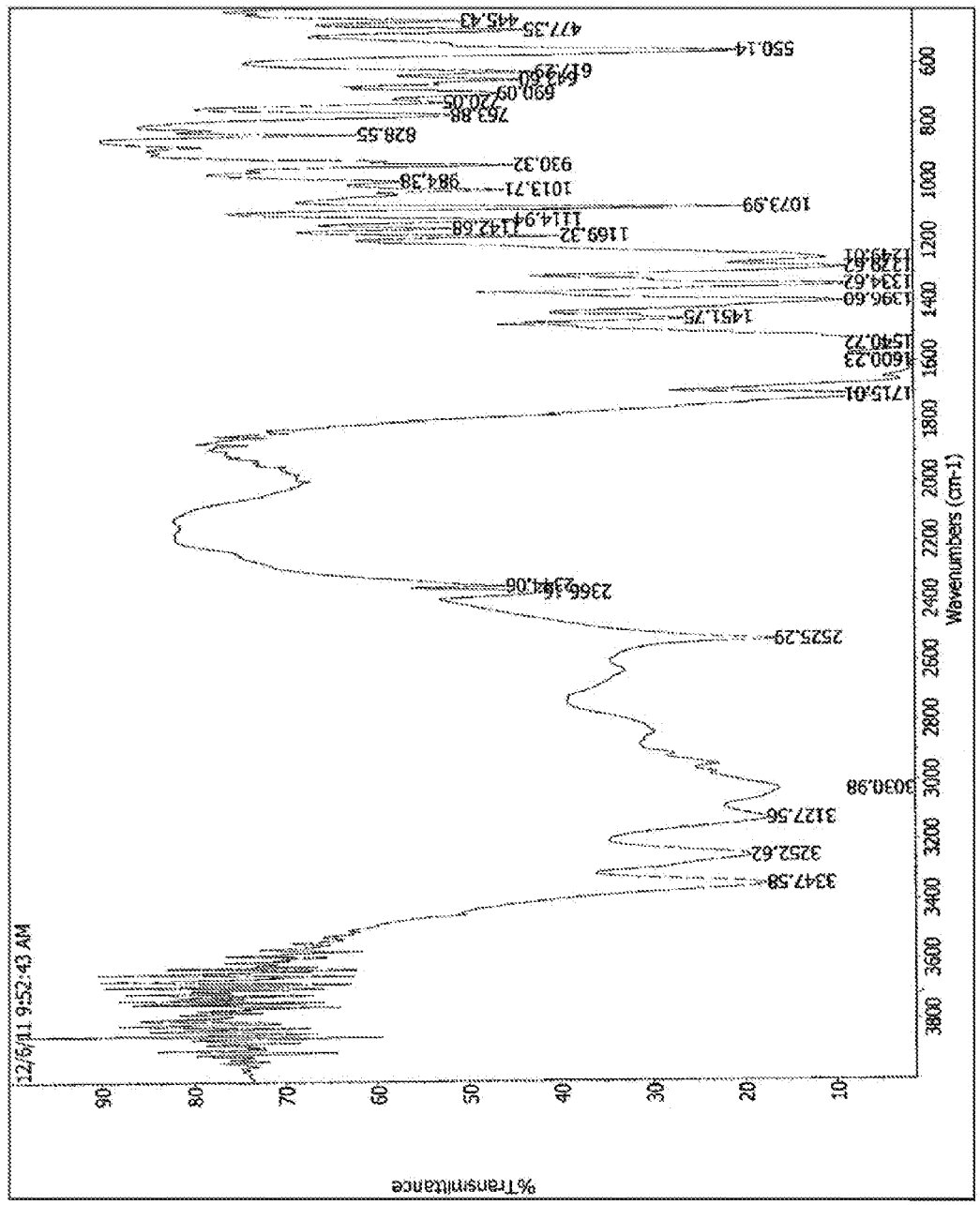
FIG. 24 illustrates an Infrared Spectrum of Glutathione.
Figure 25:
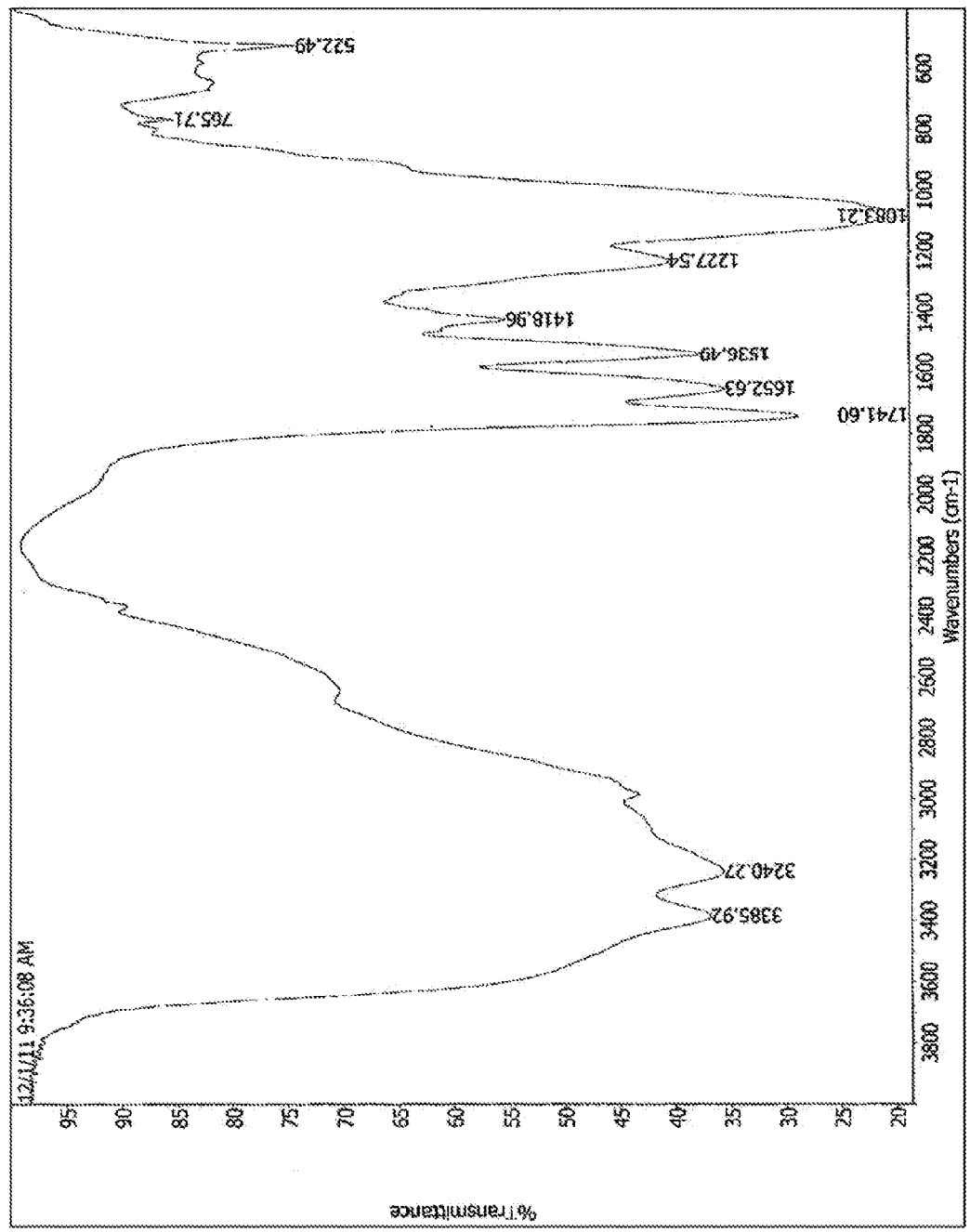
FIG. 25 illustrates an Infrared Spectrum of Glutathione-functionalized Polyhydroxylated Fullerene.

Preparation of a Glutathione-Functionalized Polyhydroxylated Fullerene 0.050 g of the polyhydroxylated fullerene produced from Example 2 was reacted with 0.102 g of glutathione, which is a peptide having the chemical formula C$_{10}$H$_{17}$N$_3$O$_6$S, and 4.0 ml of boron trifluoride, in the form of boron trifluoride etherate (48% BF$_3$ by mass). The mixture of fullerene and glutathione was flushed with nitrogen, sealed, and heated with constant stirring at a temperature in the range from about 50° C. to about 65° C. for a period of about five days. The reaction mixture became a homogeneous suspension. The reaction mixture was then cooled. 25 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, a glutathione-functionalized polyhydroxylated fullerene, had a formula of C$_{60}$(OH)$_x$(C$_{10}$H$_{17}$N$_3$O$_6$S)$_y$, wherein y is about 4.5, and wherein x is in the range from about 24 to about 40. Elemental analysis yielded the following results: % C 34.91, % H 4.17, % S 5.46, % N 6.9. FIG. 24 illustrates the infrared spectrum of glutathione C$_{10}$H$_{17}$N$_3$O$_6$S. FIG. 25 illustrates the infrared spectrum of glutathione-functionalized polyhydroxylated fullerene C$_{60}$(OH)$_x$(C$_{10}$H$_{17}$N$_3$O$_6$S)$_y$, wherein y is about 4.5, and wherein x is in the range from about 24 to about 40.

Example 14

Figure 26:
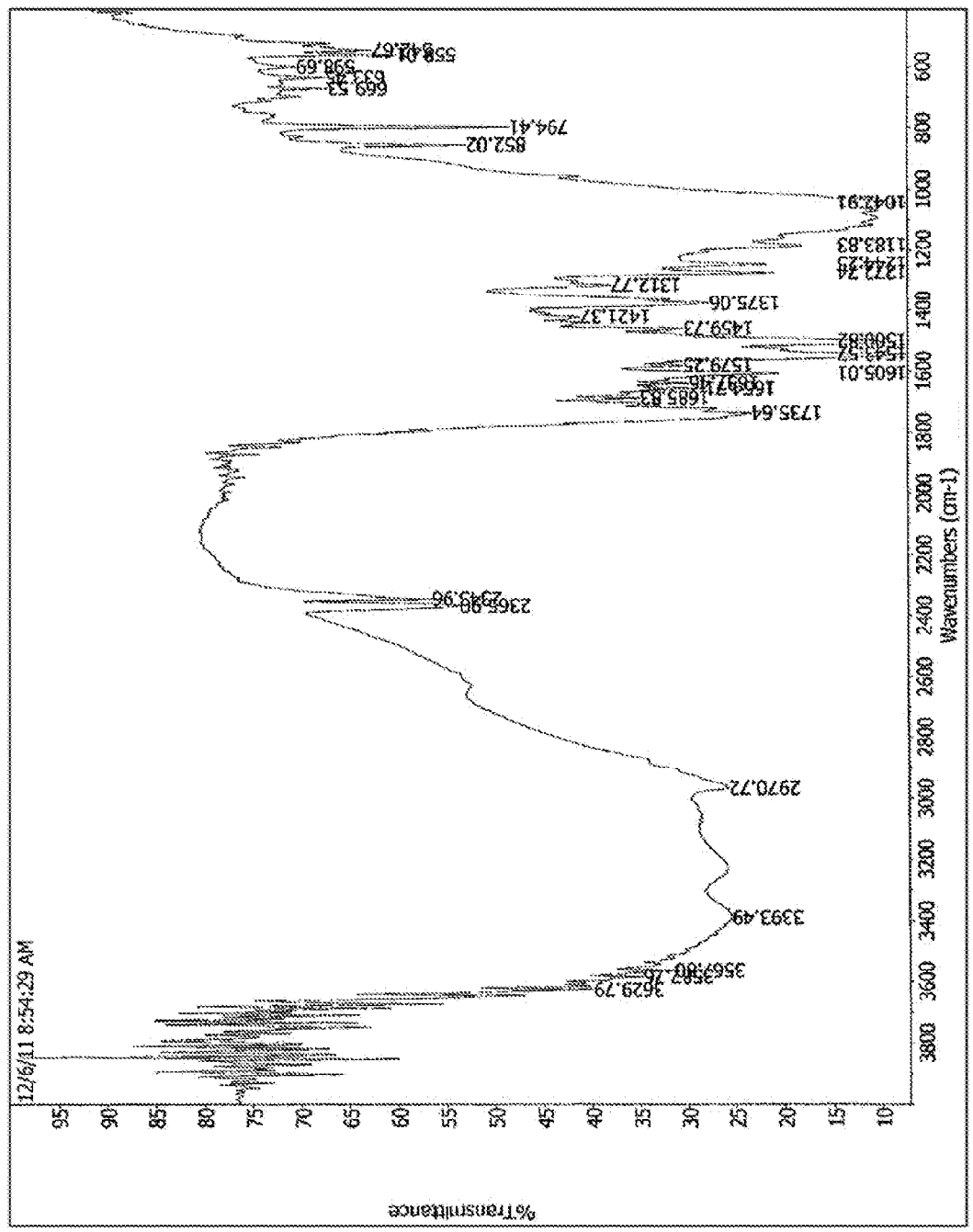
FIG. 26 illustrates an Infrared Spectrum of Avobenzone/Glutathione-functionalized Polyhydroxylated Fullerene.
Figure 27:
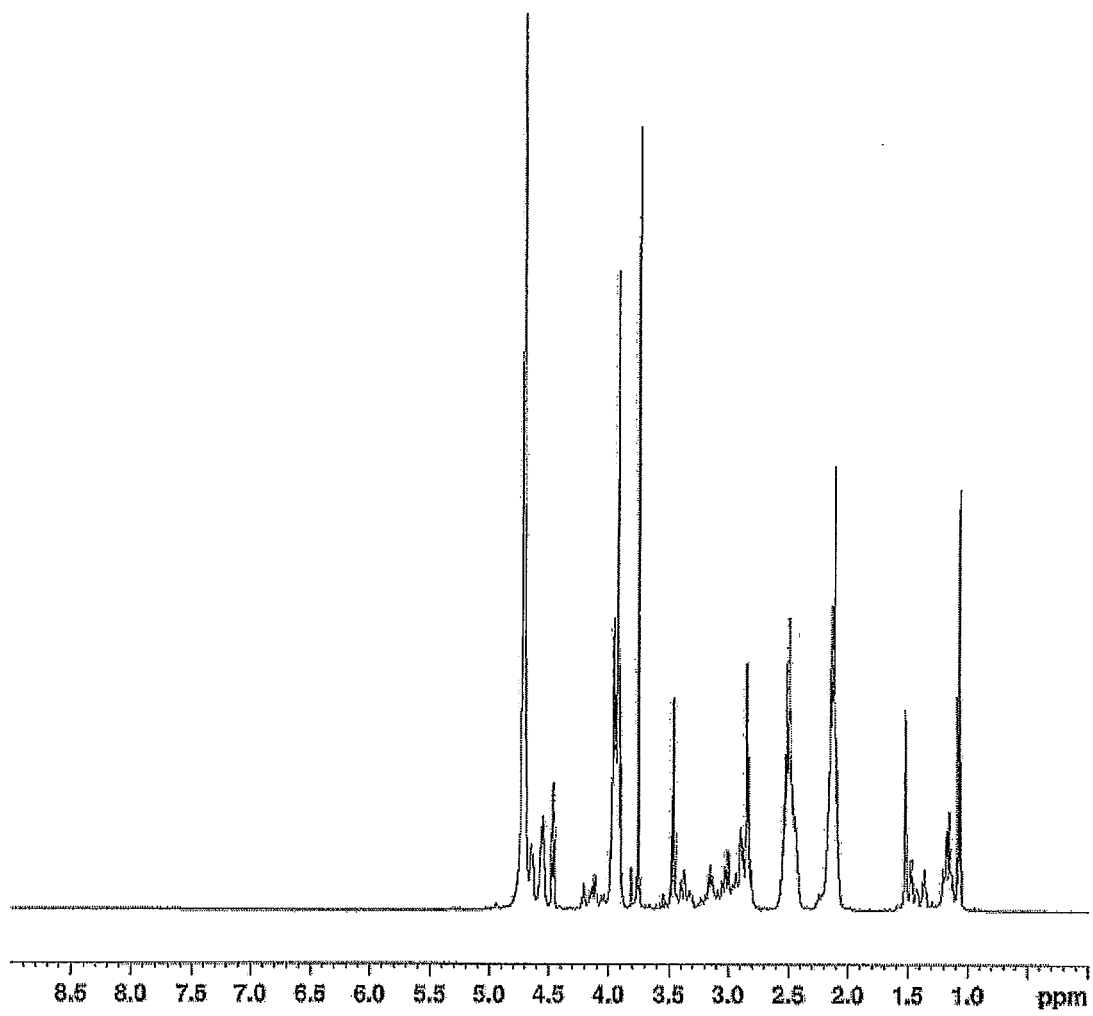
FIG. 27 illustrates the Proton NMR spectrum of Avobenzone/Glutathione-functionalized Polyhydroxylated Fullerene.
Figure 28A:
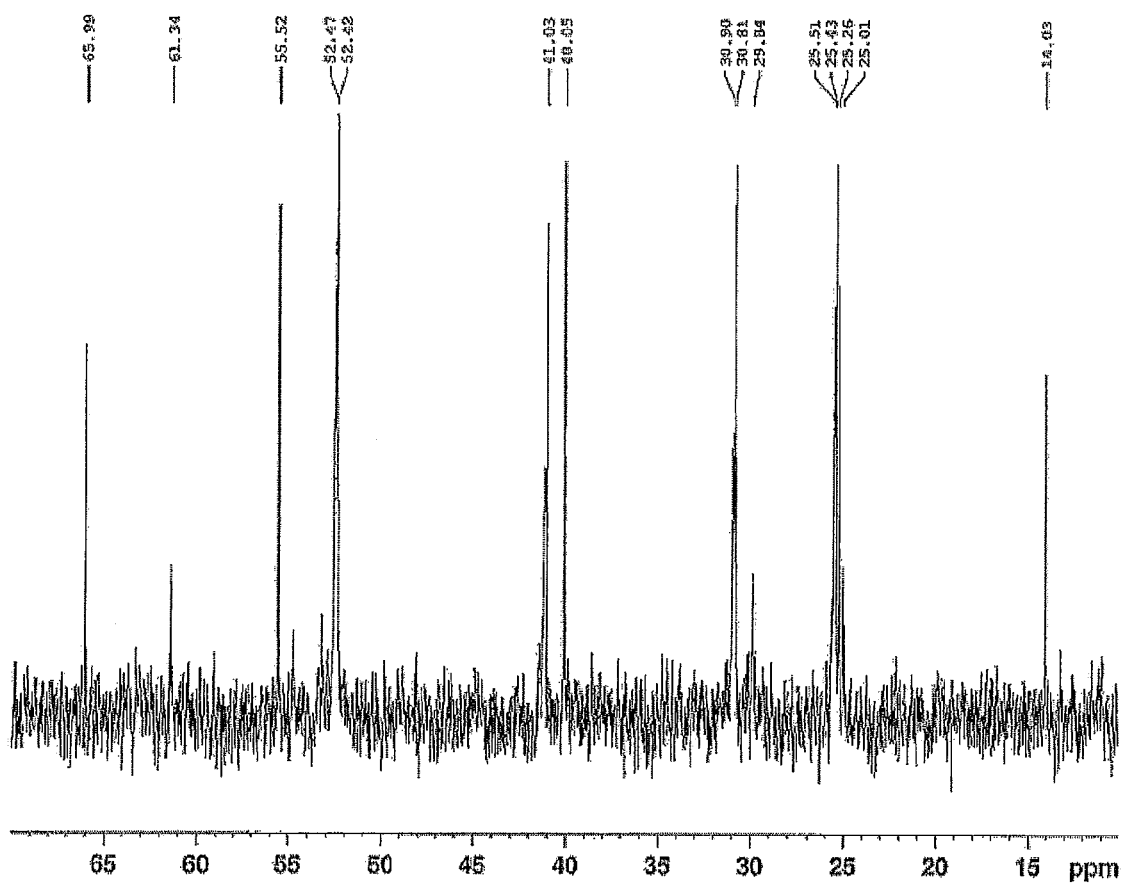
FIG. 28a illustrates a first portion of the Carbon NMR Spectrum of Avobenzone/Glutathione-functionalized Polyhydroxylated Fullerene.
Figure 28B:
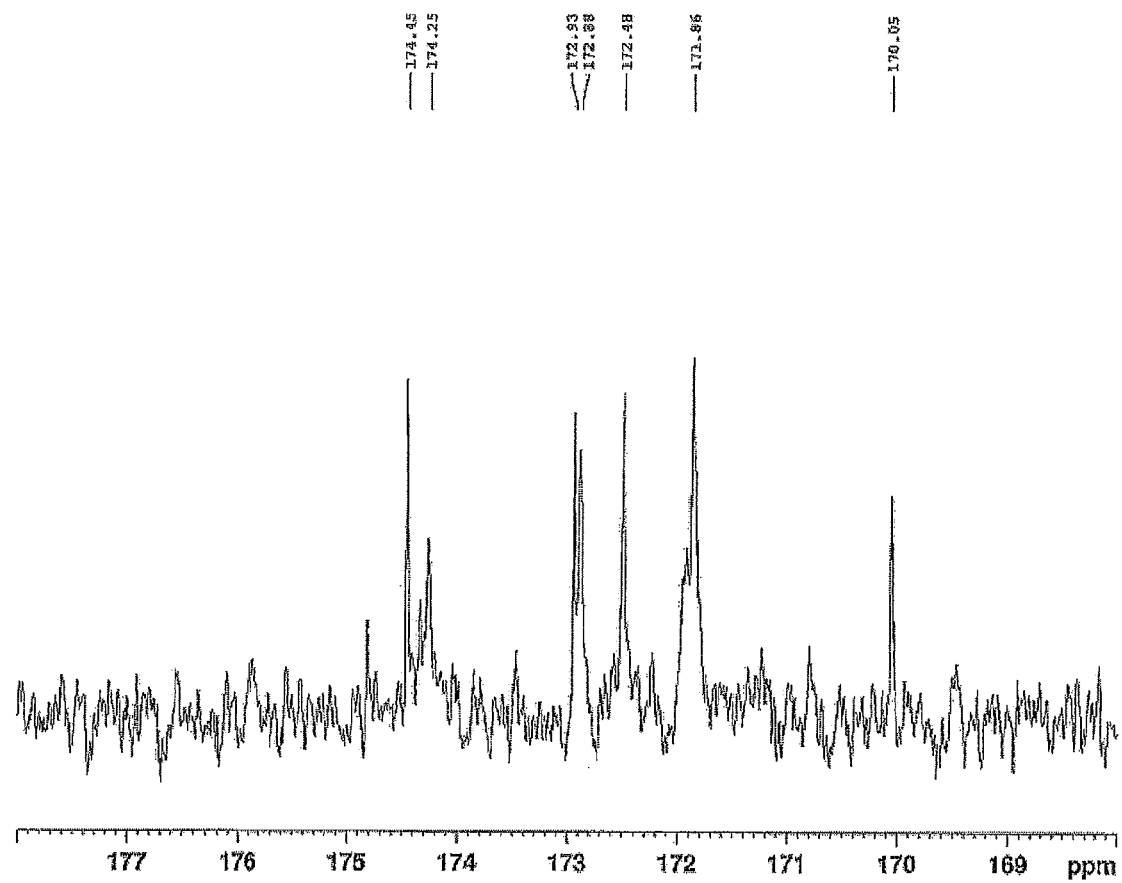
FIG. 28b illustrates a second portion of the Carbon NMR Spectrum of Avobenzone/Glutathione-functionalized Polyhydroxylated Fullerene.

Preparation of an Avobenzone/Glutathione-Functionalized Polyhydroxylated Fullerene 0.050 g of the polyhydroxylated fullerene produced from Example 2 was reacted with 0.050 g of avobenzone, 0.053 g of glutathione, and 4.0 ml of boron trifluoride, in the form of boron trifluoride etherate (48% BF$_3$ by mass). The mixture of fullerene, avobenzone, and glutathione was flushed with nitrogen, sealed, and heated with constant stirring at a temperature in the range from about 50° C. to about 65° C. for a period of about five days. The reaction mixture became a homogeneous suspension. The reaction mixture was then cooled. 25 ml of diethyl ether was then added to the homogeneous suspension. The reaction mixture was then chilled in a freezer at −20° C. and the product, in the form of a solid, was isolated using ultracentrifugation. Using a combination of elemental analysis and infrared spectroscopy, it was determined that the resulting product, an avobenzone/glutathione-functionalized polyhydroxylated fullerene, had a formula of $C_{60}(OH)_x(C_{20}H_{22}O_3)_y(C_{10}H_{17}N_3O_6S)_z$ wherein y is about 1 and z is about 3 and wherein x is in the range from about 24 to about 40. Elemental analysis yielded the following results: % C 42.9, % H 4.19, % S 3.55, % N 4.27. Proton NMR and carbon NMR further demonstrated that both avobenzone and glutathione were attached to the fullerenol. FIG. 26 illustrates the infrared spectrum of avobenzone/glutathione-functionalized polyhydroxylated fullerene $C_{60}(OH)_x(C_{20}H_{22}O_3)_y(C_{10}H_{17}N_3O_6S)_z$ wherein y is about 1 and z is about 3, and wherein x is in the range from about 24 to about 40. FIG. 27 illustrates the proton NMR spectrum of avobenzone/glutathione-functionalized polyhydroxylated fullerene. FIG. 28a illustrates a first region of the carbon NMR spectrum of avobenzone/glutathione-functionalized polyhydroxylated fullerene. FIG. 28b illustrates different regions of the carbon NMR spectrum of avobenzone/glutathione-functionalized polyhydroxylated fullerene.

Example 15

Evaluation of Anti-Oxidant Activity of Commercial Anti-Oxidants and Their-Functionalized Fullerenol Derivatives Several anti-oxidant compounds including linoleic acid, linolenic acid, Coenzyme $Q_{10}$, arachidonic acid, a fullerenol, and fullerenols which had been functionalized with linoleic acid, linolenic acid, Coenzyme $Q_{10}$, arachidonic acid, and an avobenzone/glutathione mixture were tested using a DPPH radical-scavenging method as described above. Stock solutions of 100 micromolar DPPH were prepared using 3.9 milligrams (mg) of DPPH dissolved in 100 milliliters (ml) of solution using spectroscopic grade methanol (MeOH). 3.5 ml of the DPPH solution was combined with 0.5 ml of test solutions of various concentrations of the anti-oxidant compounds. The commercial anti-oxidants, which are not water soluble, were dissolved in MeOH while their functionalized fullerene derivatives were dissolved in distilled water. The test mixture was immediately placed in a spectrometer which measured the absorbance of the mixture at 517 nm at various intervals over periods of 6 to 8 hours. Typically 4 or more samples of the anti-oxidants at various concentrations were tested. The concentrations, expressed in milligrams per milliliter (mg/ml), were selected so that some of the samples would consume more than 50% of the DPPH and others would not.

The percent of DPPH remaining at a given time interval was calculated using the following equation:

$$\% \ DPPH_{rem} = \frac{A_{C_t} + (A_{DPPH_i} - A_{DPPH_{t'}})}{A_{DPPH_i}}$$

$A_{C_t}$ is the absorbance value to the compound/DPPH solution at time t, $A_{DPPH_i}$ is the initial value of the DPPH control blank at time t=0, and $A_{DPPH_{t'}}$ is the absorbance value of the control blank DPPH at time t=t'. The term $(A_{DPPH_t} - A_{DPPH_{t'}})$ in the above equation is the absorbance correction factor for DPPH radical decay as measured in the control blank.

The % $DPPH_{ram}$ was recorded for each of the four concentrations at two different reaction times (30 minutes and 300 minutes). The % $DPPH_{ram}$ was converted to milligrams (mg) of DPPH remaining and plotted as a function of milligrams (mg) of compound for each of the two reaction times. Linear regressions were calculated for each of the data sets according to the following formula:

$$C_{DPPH} = m_t \cdot C_c + C_{DPPH_o}$$

$C_{DPPH}$ is the mass of DPPH remaining at time t=30 minutes and time t=300 minutes, $C_o$ is the mass of the compound in the cuvette, $C_{DPPH_o}$ is the initial concentration of the DPPH in the cuvette, and $m_t$ is the slope determined by the linear regression. The slope was used as a parameter to estimate the anti-oxidant potential of the compound. Preliminary experiments verified that varying the initial mass of DPPH in the cuvette did not affect the reaction rate $(m_t)$, that is, the reaction rate is independent of the DPPH concentration. FIGS. 30-34 illustrate the slope (anti-oxidant potential) of commercial anti-oxidants and their functionalized fullerenol derivatives (indicated with FF in the legends).

The slope for each compound was tabulated and the amount (mg) of compound needed to deplete 0.05 mg of DPPH was calculated (see Table 1). These results were used to compare the anti-oxidant potential of various compounds.

TABLE 1

| | 30 minutes | | 300 minutes | |
|---|---|---|---|---|
| Compound | Slope (mg/mg) | RD (.05 mg)* | Slope (mg/mg) | RD (.05 mg)* |
| Linoleic Acid | −0.000008 | 6250.00 | −0.0005 | 100.00 |
| Linoleic Acid Fuctionalized Fullerene | −0.0615 | 0.81 | −0.1012 | 0.49 |
| Linolenic Acid | −0.0002 | 250.00 | −0.0011 | 45.45 |
| Linolenic Acid Fuctionalized Fullerene | −0.0535 | 0.93 | −0.0905 | 0.55 |
| Coenzyme Q10 | −0.0004 | 125.00 | −0.0021 | 23.81 |
| Coenzyme Q10 Fuctionalized Fullerene | −0.0700 | 0.71 | −0.1111 | 0.45 |
| Arachidonic Acid | −0.0002 | 250.00 | −0.0011 | 45.45 |
| Arachidonic Acid Fuctionalized Fullerene | −0.0994 | 0.50 | −0.1710 | 0.29 |
| Glutathione Avobenzone Func. Fullerene | −0.0650 | 0.77 | −0.1584 | 0.32 |
| Polyhydroxylated Fullerene | −0.0091 | 5.49 | −0.0192 | 2.60 |

*Note:
RD(.05 mg) is the amount of compound in (mg) needed to deplete .05 mg of DPPH As illustrated in Table 1, the anti-oxidant-functionalized fullerenols were significantly better at consuming DPPH free radicals than the anti-oxidants were by themselves. That is, a much lower amount of the anti-oxidant-functionalized fullerenols were needed to deplete 0.05 mg of DPPH. Thus, the anti-oxidant-functionalized fullerenols described herein have superior anti-oxidant capabilities.

Example 16

Evaluation of UV Absorbing Ability of an Avobenzone/Glutathione-Functionalized Polyhydroxylated Fullerene 5.0 milligrams (mg) of avobenzone, a UV light absorbing substance widely used in sunscreens, was dissolved in 10 milliliters (ml) of reagent grade acetone. 5.0 milligrams (mg) of an avobenzone/glutathione-functionalized polyhydroxylated fullerene was dissolved in 10 milliliters (ml) of distilled water. UV absorbance (A) of the resulting solutions was measured at 290 nm, 320 nm, and 400 nm. Table 2 shows the absorbance (A) of avobenzone and avobenzone/glutathione-functionalized polyhydroxylated fullerene at the various wavelengths.

TABLE 2

| Compound | Concentration (mg/ml) | Absorbance (A) | | |
|---|---|---|---|---|
| | | 290 nm | 320 nm | 400 nm |
| Avobenzone | 0.5 | 0.297 | 0.521 | 0.376 |
| Avobenzone/Glutathione-functionalized fullerene | 0.5 | 1.397 | 0.933 | 0.293 |

As shown in Table 2, the UV absorbing ability of avobenzone/glutathione-functionalized fullerene is effective for both UV A (400-315 nm) and UV B (315-280 nm) regions of the ultraviolet spectrum. It can further be seen that the avobenzone/glutathione-functionalized fullerene exceeds the UV absorbing power of commercial avobenzone in the crucial UV B region. Based on the above data, an avobenzone/glutathione-functionalized fullerene possesses enhanced UV absorbing abilities in the UV B region.

Example 17

Preparation of a Polyhydroxylated Fullerene

About 0.300 grams a $C_{60}$ fullerene were reacted with 20 ml of aqueous concentrated hydrogen peroxide (50% $H_2O_2$ by mass). The reaction mixture was stirred vigorously at 70° C. for a period of five days. The mixture turned reddish brown indicating that a reaction occurred. In additional examples, the above reaction is conducted with a fullerene or, for at least ten days, including 10 days, 14 days and 21 days, at various temperatures in the range of 60° C. to 80° C.

To isolate the polyhydroxylated fullerene product, the reaction mixture is then added to a mixture of isopropanol, hexane, and diethyl ether in a ratio of 10:12:7 to cause a precipitate, in the form of solid crystals, to form. After ultracentrifugation and decantation, the solid crystals are isolated. The identity of the product as a polyhydroxylated fullerene is confirmed using a combination of elemental analysis and infrared spectroscopy.

While the preferred embodiments of the present invention are described above, obvious modifications and alterations of the present invention may be made without departing from the spirit and scope of the present invention. The scope of the present invention is defined in the appended claims and equivalents thereto.

The invention claimed is:

1. A water-soluble functionalized polyhydroxylated fullerene having the general formula: $R—(R')_y(OH)_x$,
    wherein R is a fullerene, R' is a functional group, x is a number of at least ⅔ the number of carbon atoms in R, and y is a number in the range from about 1% to about 7% of the number of carbon atoms in R, and
    wherein R' is chosen from prednisone, arachidonic acid, biotin, avobenzone, glutathione, propanil, hydrocortisone, linoleic acid, α-linolenic acid, Coenzyme $Q_{10}$, an avobenzone/glutathione mixture, and mixtures thereof.

2. The water-soluble fullerene according to claim 1, wherein R' is prednisone.

3. The water-soluble fullerene according to claim 1, wherein R' is arachidonic acid.

4. The water-soluble fullerene according to claim 1, wherein R' is biotin.

5. The water-soluble fullerene according to claim 1, wherein R' is avobenzone.

6. The water-soluble fullerene according to claim 1, wherein R' is glutathione.

7. The water-soluble fullerene according to claim 1, wherein R' is propanil.

8. The water-soluble fullerene according to claim 1, wherein R' is hydrocortisone.

9. The water-soluble fullerene according to claim 1, wherein R' is linoleic acid.

10. The water-soluble fullerene according to claim 1, wherein R' is α-linolenic acid.

11. The water-soluble fullerene according to claim 1, wherein R' is Coenzyme $Q_{10}$.

12. The water-soluble fullerene according to claim 1, wherein R' is a mixture of avobenzone and glutathione.

* * * * *